(12) United States Patent
Park et al.

(10) Patent No.: US 7,968,579 B2
(45) Date of Patent: Jun. 28, 2011

(54) ANTIFUNGAL TRIAZOLE DERIVATIVES

(75) Inventors: Joon Seok Park, Yongin-si (KR); Kyung A Yu, Suwon-si (KR); Sun Young Kim, Seoul (KR); Yeon Jung Song, Suwon-si (KR); Kang-Pil Kim, Seoul (KR); Yun Soo Yoon, Seoul (KR); Mi Ryeong Han, Anyang-si (KR)

(73) Assignee: Daewoong Pharmaceutical Co., Ltd., Sungnam-si (KR)

( * ) Notice: Subject to any disclaimer, the term of this patent is extended or adjusted under 35 U.S.C. 154(b) by 174 days.

(21) Appl. No.: 12/092,156

(22) PCT Filed: Oct. 31, 2006

(86) PCT No.: PCT/KR2006/004495
§ 371 (c)(1),
(2), (4) Date: Apr. 30, 2008

(87) PCT Pub. No.: WO2007/052943
PCT Pub. Date: May 10, 2007

(65) Prior Publication Data
US 2008/0287440 A1    Nov. 20, 2008

(30) Foreign Application Priority Data
Oct. 31, 2005 (KR) .......................... 10-2005-0103142

(51) Int. Cl.
*A61K 31/41* (2006.01)
*C07D 207/00* (2006.01)

(52) U.S. Cl. ..................... 514/383; 514/403; 548/262.2; 548/356.1

(58) Field of Classification Search ................... 514/383, 514/403; 548/262.2, 356.1
See application file for complete search history.

(56) References Cited

U.S. PATENT DOCUMENTS

| | | | | |
|---|---|---|---|---|
| 4,404,216 A | * | 9/1983 | Richardson | 514/383 |
| 4,587,239 A | * | 5/1986 | Regel et al. | 514/184 |
| 5,371,100 A | * | 12/1994 | Itoh et al. | 514/381 |
| 5,495,024 A | * | 2/1996 | Itoh et al. | 548/267.8 |

FOREIGN PATENT DOCUMENTS

| | | |
|---|---|---|
| EP | 0121888 A2 | 10/1984 |
| EP | 234499 A2 | 9/1987 |
| EP | 548553 A1 | 6/1993 |
| WO | 01/79196 A2 | 10/2001 |

OTHER PUBLICATIONS

Patini, et al., Chem. Rev., 96(8), 1996, pp. 3147-3176.*
European Search Report issued in corresponding EP Application No. 06812334.8, dated Nov. 15, 2010.

* cited by examiner

*Primary Examiner* — Susannah Chung
(74) *Attorney, Agent, or Firm* — Sughrue Mion, PLLC

(57) ABSTRACT

Disclosed herein are antifungal triazole derivatives or pharmaceutically acceptable salts thereof, a preparation method thereof, and a pharmaceutical composition comprising the same. The triazole derivatives of Chemical Formula 1 or pharmaceutically acceptable salts thereof according to the present invention have excellent inhibitory activity against a broad spectrum of fungi, in addition to being safe to the body, and thus are very useful in the treatment and prevention of fungal infection.

13 Claims, No Drawings

ANTIFUNGAL TRIAZOLE DERIVATIVES

This is a National Stage application under 35 U.S.C. §371 of PCT/KR2006/004495 filed on Oct. 31, 2006, which claims benefit from Korean Patent Application 10-2005-0103142 filed on Oct. 31, 2005, all of which are incorporated herein by reference.

TECHNICAL FIELD

The present invention relates, in general, to novel antifungal triazole derivatives and, more particularly, to highly fungicidal triazole derivatives having phenyl-pyrazole groups, and pharmaceutically acceptable salts thereof. Also, the present invention is concerned with a method for preparing the novel triazole derivatives and the use of the triazole derivatives in the treatment of fungal diseases.

BACKGROUND ART

Recently, cancer patients undergoing chemical therapy, patients who receive organ implants, and patients with HIV or AIDS have been reported to be at an increasingly great risk of fungal infection, mostly from opportunistic pathogens, such as *Candida* spp., *Aspergillus* spp. and *Cryptococcus neoformans*. Currently commercially available antifungal agents against these pathogens suffer from disadvantages of toxicity to the body and therapeutic activity against a narrow range of fungi. As patients having low immunity are currently increasing in number and contracting serious fungal infections, there is an increasing demand for antifungal agents that have excellent inherent pharmacokinetic characteristics and potent inhibitory activities against a broad spectrum of fungi.

A number of derivatives having antifungal activity are known, and have been developed for the treatment of mammals, including humans, infected with fungi. For example, orally available triazole derivatives were reported in the late 1980s, and are represented by Fluconazole (GB Pat. No. 2099818), Itraconazole (U.S. Pat. No. 4,267,179) and particularly, Voriconazole (EU Pat. No. 0440372). None of them, however, are sufficiently satisfactory for use as medicine in that they do not exhibit all of excellent inhibitory activity against some of the opportunistic fungi which cause fatal infections in patients having decreased immunity, good safety, and suitable pharmacokinetics within the body. There is therefore a need for a compound that is highly safe and easily absorbed by the body and has highly potent fungicidal activity.

Many of the antifungal agents which have been developed or are now under study have been found to have additional heterocyclic substituents plus triazole. For instance, fluconazole has a five-membered heterocyclic compound, while a six-membered heterocyclic ring is contained in voriconazole. In addition, isoxazole (EU Pat. No. 0241232, Shionogi Co.) and triazolone (EU Pat. No. 0659751, Takeda Co.) have respective five-membered heterocyclic compounds. Pyrazole rings are found in the compounds disclosed in JP 3415865 by Takeda Co., in WO 2001/79196 by Basilea Co. and in EP 0308782 by Bayer Co. The compounds of the above-mentioned patents are, however, different in structure and antifungal activity from the substituted phenyl-pyrazole derivatives of the present invention. Substituted pyrazole derivatives are also known to have antifungal activity (U.S. Pat. No. 5,705,453, EU Pat. Nos. 1171437, 0308782 and 0234499). Nowhere are triazole derivatives having substituted phenyl-pyrazole structures according to the present invention disclosed in these patents. The conventional compounds are quite different in chemical structure from the compounds of the present invention.

DISCLOSURE OF THE INVENTION

It is an object of the present invention to provide novel antifungal triazole derivatives having substituted phenyl-pyrazole groups, represented by the following chemical formula 1, or pharmaceutically acceptable salts thereof.

It is another object of the present invention to provide a method for preparing the novel antifungal triazole derivatives and antifungal compositions comprising the triazole derivatives or pharmaceutically acceptable salts thereof as active ingredients.

BEST MODE FOR CARRYING OUT THE INVENTION

In one embodiment, the present invention pertains to a triazole derivative having the following chemical formula 1, and a pharmaceutically acceptable salt thereof.

[Chemical Formula 1]

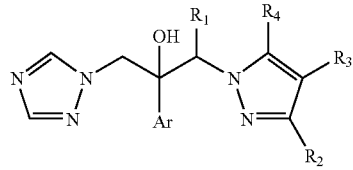

wherein,

Ar is $C_6$-$C_{20}$ aryl substituted with at least one halogen or trifluoromethyl group;

$R_1$ is hydrogen, fluorine, or $C_1$-$C_4$ lower alkyl;

$R_2$, $R_3$ and $R_4$ may be different or the same and are each hydrogen; halogen; $C_1$-$C_4$ lower alkyl; $C_1$-$C_4$ alkoxy; $C_1$-$C_4$ haloalkyl; $C_3$-$C_6$ cycloalkyl; nitro; cyano; amino; hydroxy; $C_6$-$C_{20}$ aryl, non-substituted or substituted with at least one radical selected from a group consisting of $C_1$-$C_4$ lower alkyl, $C_1$-$C_4$ alkoxy, halogen, cyano, nitro, $C_1$-$C_4$ haloalkyl, $C_1$-$C_4$ haloalkoxy, morpholine, pyrrolidine, piperidine,

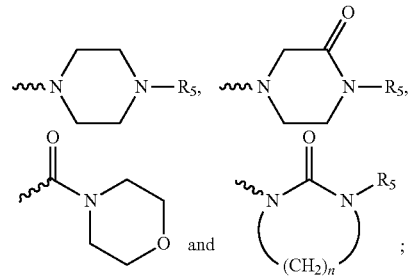

or $C_6$-$C_{20}$ heteroaryl, non-substituted or substituted with at least one substituent selected from a group consisting of $C_1$-$C_4$ lower alkyl, $C_1$-$C_4$ alkoxy, halogen, cyano, nitro, $C_1$-$C_4$ haloalkyl, and $C_1$-$C_4$ haloalkoxy, $R_5$ is hydrogen, $C_1$-$C_4$ alkyl, $C_1$-$C_4$ alkoxy or $C_1$-$C_5$ hydroxy alkyl, and n is an integer of 1 to 3.

In the Chemical Formula 1, preferably,

Ar is phenyl substituted with at least one halogen, $R_1$ is a $C_1$-$C_4$ lower alkyl, $R_2$, $R_3$ and $R_4$ may be different or the same, and are each hydrogen; $C_1$-$C_4$ lower alkyl; $C_1$-$C_4$ haloalkyl; nitro; cyano; amino; hydroxy; phenyl, non-substituted or substituted with at least one radical selected from a group consisting of $C_1$-$C_4$ lower alkyl, $C_1$-$C_4$ alkoxy, halogen, cyano, nitro, trifluoromethyl, trifluoromethoxy, morpholine, pyrrolidine,

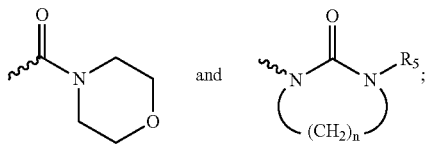

or heteroaryl selected from among pyridine, pyrimidine, quinoline, quinoxaline and benzofuran, said heteroaryl being non-substituted or substituted with at least one radical selected from a group consisting of $C_1$-$C_4$ lower alkyl, $C_1$-$C_4$ alkoxy, halogen, cyano, nitro, trifluoromethyl and trifluoromethoxy, $R_5$ is hydrogen, $C_1$-$C_4$ alkyl, or $C_1$-$C_5$ hydroxy alkyl, and n is an integer of 2 or 3.

Concrete examples of more preferable compounds according to Chemical Formula 1 include (2R,3R)-3-(3-(2-bromophenyl)-1H-pyrazole-1-yl)-2-(2,4-difluorophenyl)-1-(1H-1,2,4-triazole-1-yl)butane-2-ol, (2R,3R)-3-(3-(3-bromophenyl)-1H-pyrazole-1-yl)-2-(2,4-difluorophenyl)-1-(1H-1,2,4-triazole-1-yl)butane-2-ol, (2R,3R)-3-(3-(4-bromophenyl)-1H-pyrazole-1-yl)-2-(2,4-difluorophenyl)-1-(1H-1,2,4-triazole-1-yl)butane-2-ol, (2R,3R)-3-(2,4-difluorophenyl)-3-(3-(4-nitrophenyl)-1H-pyrazole-1-yl)-1-(1H-1,2,4-triazole-1-yl)butane-2-ol, 4-(1-((2R,3R)-3-(2,4-difluorophenyl)-3-hydroxy-4-(1H-1,2,4-triazole-1-yl)butane-2-yl)-1H-pyrazole-3-yl) benzonitrile, (2R,3R)-3-(4-phenyl)-1H-pyrazole-1-yl)-2-(2,4-difluorophenyl)-1-(1H-1,2,4-triazole-1-yl)butane-2-ol, (2R,3R)-3-(4-(2-fluorophenyl)1H-pyrazole-1-yl)-2-(2,4-difluorophenyl)-1-(1H-1,2,4-triazole-1-yl)butane-2-ol, (2R,3R)-3-(4-(2-chlorophenyl)-1H-pyrazole-1-yl)-2-(2,4-difluorophenyl)-1-(1H-1,2,4-triazole-1-yl)butane-2-ol, (2R,3R)-3-(4-(2-bromophenyl)-1H-pyrazole-1-yl)-2-(2,4-difluorophenyl)-1-(1H-1,2,4-triazole-1-yl)butane-2-ol, 2-(1-((2R,3R)-3-(2,4-difluorophenyl)-3-hydroxy-4-(1H-1,2,4-triazole-1-yl)butane-2-yl)-1H-pyrazole-4-yl)benzonitrile, (2R,3R)-2-(2,4-difluorophenyl)-3-(4-(2-nitrophenyl)-1H-pyrazole-1-yl)-1-(1H-1,2,4-triazole-1-yl)butane-2-ol, (2R,3R)-3-(4-(3-fluorophenyl)-1H-pyrazole-1-yl)-2-(2,4-difluorophenyl)-1-(1H-1,2,4-triazole-1-yl)butane-2-ol, (2R,3R)-3-(4-(3-chlorophenyl)-1H-pyrazole-1-yl)-2-(2,4-difluorophenyl)-1-(1H-1,2,4-triazole-1-yl)butane-2-ol, (2R,3R)-3-(4-(3-bromophenyl)-1H-pyrazole-1-yl)-2-(2,4-difluorophenyl)-1-(1H-1,2,4-triazole-1-yl)butane-2-ol, (2R,3R)-3-(4-(3-trifluoromethyl)phenyl)-1H-pyrazole-1-yl)-2-(2,4-difluorophenyl)-1-(1H-1,2,4-triazole-1-yl)butane-2-ol, 3-(1-((2R,3R)-3-(2,4-difluorophenyl)-3-hydroxy-4-(1H-1,2,4-triazole-1-yl)butane-2-yl)benzonitrile, (2R,3R)-2-(2,4-difluorophenyl)-3-(4-(3-nitrophenyl)-1H-pyrazole-1-yl)-1-(1H-1,2,4-triazole-1-yl)butane-2-ol, (2R,3R)-3-(4-(4-fluorophenyl)-1H-pyrazole-1-yl)-2-(2,4-difluorophenyl)-1-(1H-1,2,4-triazole-1-yl)butane-2-ol, (2R,3R)-3-(4-(4-chlorophenyl)-1H-pyrazole-1-yl)-2-(2,4-difluorophenyl)-1-(1H-1,2,4-triazole-1-yl)butane-2-ol, (2R,3R)-3-(4-(4-bromophenyl)-1H-pyrazole-1-yl)-2-(2,4-difluorophenyl)-1-(1H-1,2,4-triazole-1-yl)butane-2-ol, (2R,3R)-2-(2,4-difluorophenyl)-3-(4-(4-methoxyphenyl)-1H-pyrazole-1-yl)-1-(1H-1,2,4-triazole-1-yl)butane-2-ol, (2R,3R)-2-(2,4-difluorophenyl)-3-(4-(4-nitrophenyl)-1H-pyrazole-1-yl)-1-(1H-1,2,4-triazole-1-yl)butane-2-ol, (2R,3R)-3-(4-(4-trifluoromethyl)phenyl)-1H-pyrazole-1-yl)-2-(2,4-difluorophenyl)-1-(1H-1,2,4-triazole-1-yl) butane-2-ol, 4-(1-((2R,3R)-3-(2,4-difluorophenyl)-3-hydroxy-4-(1H-1,2,4-triazole-1-yl)butane-2-yl)-1H-pyrazole-4-yl) benzonitrile, (2R,3R)-2-(2,4-difluorophenyl)-1-(1H-1,2,4-triazole-1-yl)-3-(4-(4-trifluoromethyl)phenyl)-1H-pyrazole-1-yl)-1-butane-2-ol, 1-(4-(1-((2R,3R)-3-(2,4-difluorophenyl)-3-hydroxy-4-(1H-1,2,4-triazole-1-yl)butane-2-yl)-1H-pyrazole-4-yl)phenyl)-3-methylimidazolidine-2-on, 1-(4-(1-((2R,3R)-3-(2,4-difluorophenyl)-3-hydroxy-4-(1H-1,2,4-triazole-1-yl)butane-2-yl)-1H-pyrazole-4-yl)phenyl)-3-isopropylimidazolidine-2-on, 3-(4-(1-((2R,3R)-3-(2,4-difluorophenyl)-3-hydroxy-4-(1H-1,2,4-triazole-1-yl)butane-2-yl)-1H-pyrazole-4-yl)phenyl)-tetrahydro-1-methylpyrimidine-2(1H)-on, (2R,3R)-3-(4-(4-fluoro-2-methylphenyl)-1H-pyrazole-1-yl)-2-(2,4-difluorophenyl)-1-(1H-1,2,4-triazole-1-yl)butane-2-ol, (2R,3R)-3-(4-(4-fluoro-3-methylphenyl)-1H-pyrazole-1-yl)-2-(2,4-difluorophenyl)-1-(1H-1,2,4-triazole-1-yl)butane-2-ol, (2R,3R)-3-(4-(4-fluoro-2-methoxyphenyl)-1H-pyrazole-1-yl)-2-(2,4-difluorophenyl)-1-(1H-1,2,4-triazole-1-yl)butane-2-ol, (2R,3R)-3-(4-(4-fluoro-3-methoxyphenyl)-1H-pyrazole-1-yl)-2-(2,4-difluorophenyl)-1-(1H-1,2,4-triazole-1-yl)butane-2-ol, (2R,3R)-3-(4-(4-chloro-2-fluorophenyl)-1H-pyrazole-1-yl)-2-(2,4-difluorophenyl)-1-(1H-1,2,4-triazole-1-yl)butane-2-ol, (2R,3R)-3-(4-(4-chloro-2-methylphenyl)-1H-pyrazole-1-yl)-2-(2,4-difluorophenyl)-1-(1H-1,2,4-triazole-1-yl)butane-2-ol, (2R,3R)-3-(4-(4-chloro-3-methylphenyl)-1H-pyrazole-1-yl)-2-(2,4-difluorophenyl)-1-(1H-1,2,4-triazole-1-yl)butane-2-ol, (2R,3R)-3-(4-(4-chloro-2-methoxyphenyl)-1H-pyrazole-1-yl)-2-(2,4-difluorophenyl)-1-(1H-1,2,4-triazole-1-yl)butane-2-ol, 2-chloro-5-(1-((2R,3R)-3-(2,4-difluorophenyl)-3-hydroxy-4-(1H-1,2,4-triazole-1-yl)butane-2-yl)-1H-pyrazole-4-yl)benzonitrile, (2R,3R)-3-(4-(4-chloro-3-nitrophenyl)-1H-pyrazole-1-yl)-2-(2,4-difluorophenyl)-1-(1H-1,2,4-triazole-1-yl)butane-2-ol, 2-fluoro-4-(1-((2R,3R)-3-(2,4-difluorophenyl)-3-hydroxyl-4-(1H-1,2,4-triazole-1-yl)butane-2-yl)-1H-pyrazole-4-yl)benzonitrile, (2R,3R)-3-(5-(2-bromophenyl)-1H-pyrazole-1-yl)-2-(2,4-difluorophenyl)-1-(1H-1,2,4-triazole-1-yl)butane-2-ol, (2R,3R)-3-(5-(3-bromophenyl)-1H-pyrazole-1-yl)-2-(2,4-difluorophenyl)-1-(1H-1,2,4-triazole-1-yl)butane-2-ol, (2R,3R)-3-(5-(4-bromophenyl)-1H-pyrazole-1-yl)-2-(2,4-difluorophenyl)-1-(1H-1,2,4-triazole-1-yl)butane-2-ol, (2R,3R)-2-(2,4-difluorophenyl)-3(4-(pyridine-2-yl)-1H-pyrazole-1-yl)-1-(1H-1,2,4-triazole-1-yl)butane-2-ol, (2R,3R)-2-(2,4-difluorophenyl)-3(4-(pyridine-3-yl)-1H-pyrazole-1-yl)-1-(1H-1,2,4-triazole-1-yl)butane-2-ol, (2R,3R)-2-(2,4-difluorophenyl)-3(4-(pyridine-4-yl)-1H-pyrazole-1-yl)-1-(1H-1,2,4-triazole-1-yl)butane-2-ol, (2R,3R)-2-(2,4-difluorophenyl)-3(4-(5-fluoropyridine-2-yl)-1H-pyrazole-1-yl)-1-(1H-1,2,4-triazole-1-yl)butane-2-ol, (2R,3R)-2-(2,4-difluorophenyl)-3(4-(5-chloropyridine-2-yl)-1H-pyrazole-1-yl)-1-(1H-1,2,4-triazole-1-yl)butane-2-ol, 6-(1-((2R,3R)-3-(2,4-difluorophenyl)-3-hydroxy-4-(1H-1,2,4-triazole-1-yl)butane-2-yl)-1H-pyrazole-4-yl)pyridine-3-carbonitrile, (2R,3R)-2-(2,4-difluorophenyl)-3-(4-(5-nitro pyridine-2-yl)-1H-pyrazole-1-yl)-1-(1H-1,2,4-triazole-1-yl)butane-2-ol, (2R,3R)-3-(4-(3-chloro-5-trifluoromethyl)pyridine-2-yl)-1H-pyrazole-1-yl)-2-(2,4-difluorophenyl)-1-(1H-1,2,4-triazole-1-yl)butane-2-ol, 6-(1-((2R,3R)-3-(2,4-difluorophenyl)-3-hydroxy-4-(1H-1,2,4-triazole-1-yl)butane-2-yl)-1H-pyrazole-4-yl)-5-methylpyridine-3-carbonitrile, (2R,3R)-3-(4-(5-chloro-3-methylpyridine-2-yl)-1H-pyrazole-1-yl)-2-(2,4-difluorophenyl)-1-(1H-1,2,4-triazole-1-yl)butane-2-ol, (2R,3R)-3-(4-(5-fluoro-3-nitropyridine-2-yl)-1H-pyrazole-1-yl)-2-(2,4-difluorophenyl)-1-(1H-1,2,4-triazole-1-yl)butane-2-ol, (2R,3R)-2-(2,4-difluorophenyl)-3-(4-(3-methyl-5-nitropyridine-2-yl)-1H-pyrazole-1-yl)-1-(1H-1,2,4-triazole-1-yl)butane-2-ol, 5-(1-((2R,3R)-3-(2,4-difluorophenyl)-3-hydroxy-4-(1H-1,2,4-triazole-1-yl)butane-2-yl)-1H-pyrazole-4-yl)pyridine-4-carbonitrile, (2R,3R)-2-(2,4-difluorophenyl)-3-(4-(4-nitropyridine-3-yl)-1H-pyrazole-1-yl)-1-(1H-1,2,4-triazole-1-yl)butane-2-ol, (2R,3R)-2-(2,4-difluorophenyl)-3-(4-(5-fluoropyridine-3-yl)-1H-pyrazole-1-yl)-1-(1H-1,2,4-triazole-1-yl)butane-2-ol, (2R,3R)-2-(2,4-difluorophenyl)-3-(4-(5-chloropyridine-3-yl)-1H-pyrazole-1-yl)-1-(1H-1,2,4-triazole-1-yl)butane-2-ol, 5-(1-((2R,3R)-3-(2,4-difluorophenyl)-3-hydroxy-4-(1H-1,2,4-triazole-1-yl)butane-2-yl)-1H-pyrazole-4-yl)pyridine-3-carbonitrile, (2R,3R)-2-(2,4-difluorophenyl)-3-(4-(4-fluoropyridine-3-yl)-1H-pyrazole-1-yl)-1-(1H-1,2,4-triazole-1-yl)butane-2-ol, (2R,3R)-2-(2,4-difluorophenyl)-3-(4-(4-chloropyridine-3-yl)-1H-pyrazole-1-yl)-1-(1H-1,2,4-triazole-1-yl)butane-2-ol, 5-(1-((2R,3R)-3-(2,4-difluorophenyl)-3-hydroxy-4-(1H-1,2,4-triazole-1-yl)butane-2-yl)-1H-pyrazole-4-yl)pyridine-4-carbonitrile, (2R,3R)-2-(2,4-difluorophenyl)-3-(4-(3-fluoropyridine-4-yl)-1H-pyrazole-1-yl)-1-(1H-1,2,4-triazole-1-yl)butane-2-ol, (2R,3R)-2-(2,4-difluorophenyl)-3-(4-(3-chloropyridine-4-yl)-1H-pyrazole-1-yl)-1-(1H-1,2,4-triazole-1-yl)butane-2-ol, 4-(1-((2R,3R)-3-(2,4-difluorophenyl)-hydroxy-4-(1H-1,2,4-triazole-1-yl)butane-2-yl)-1H-pyrazole-4-yl)pyridine-3-carbonitrile, (2R,3R)-2-(2,4-difluorophenyl)-3-(4-(3,5-difluoropyridine-4-yl)-1H-pyrazole-1-yl)-1-(1H-1,2,4-triazole-1-yl butane-2-ol, (2R,3R)-2-(2,4-difluorophenyl)-3-(4-(pyridine-4-yl)-1H-pyrazole-1-yl)-1-(1H-1,2,4-triazole-1-yl)butane-2-ol, (2R,3R)-2-(2,4-difluorophenyl)-3-(4-(quinoline-4-yl)-1H-pyrazole-1-yl)-1-(1H-1,2,4-triazole-1-yl)butane-2-ol, (2R,3R)-2-(2,4-difluorophenyl)-3-(4-(quinoxaline-3-yl)-1H-pyrazole-1-yl)-1-(1H-1,2,4-triazole-1-yl)butane-2-ol, and (2R,3R)-3-(4-(benzofuran-2-yl)-1H-pyrazole-1-yl)-2-(2,4-difluorophenyl)-1-(1H-1,2,4-triazole-1-yl)butane-2-ol.

The term "halogen" or "halo", as used herein, represents halogen atoms, including fluorine, chlorine, bromine, or iodine atoms.

Unless otherwise specified, the term "alkyl", as used herein, means a straight or branched saturated hydrocarbon radical having 1 to 4 carbon atoms, exemplified by methyl, ethyl, propyl, isopropyl, butyl, isobutyl, sec-butyl or tert-butyl.

Unless otherwise specified, the term "haloalkyl", as used herein, means a radical in which one or more hydrogen atoms of the alkyl group (as defined above) are replaced with one or more identical or different halogen atoms, examples of which include trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2,3,3,3-pentafluoropropyl, heptafluoropropyl, 4-chlorobutyl, 4-fluorobutyl, 4-iodobutyl and 4-bromobutyl.

As used herein, the term "cycloalkyl", unless otherwise specified, means a saturated cyclic hydrocarbon radical having 3 to 6 carbon atoms, exemplified by cyclopropyl, cyclobutyl, cyclopentyl or cyclohexyl.

As used herein, the term "alkoxy", unless otherwise specified, means O-alkyl (the alkyl moiety is as defined above), exemplified by methoxy, ethoxy, propoxy, isopropoxy, butoxy, isobutoxy, sec-butoxy, tert-butoxy and the like.

By the term "haloalkoxy", unless otherwise specified, as used herein, is meant an alkoxy radical (as defined above) substituted with one or more identical or different hydrogen atoms. Examples thereof include trifluoromethoxy, fluoromethoxy, 2-chloroethoxy, 2-fluoroethoxy, 2,2-difluoroethyl, 2-iodoethoxy, 2,2-difluoroethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy and 4-chlorobutoxy.

By the term "aryl", as used herein, is meant an aromatic hydrocarbon radical such as phenyl or naphthyl, unless otherwise stated.

The compound of Chemical Formula 1 according to the present invention contains two chiral centers at the $C_2$ and $C_3$ positions. The compounds useful in the present invention are optically pure with a conformation of (2R,3R)-enantiomer. Therefore, it should be understood that the compound of the present invention includes all possible stereoisomers of (2R,3R)-enantiomers, unless otherwise specified.

As for the pharmaceutically acceptable salts of the compound of Chemical Formula 1, they may comprise inorganic or organic salts known in the antifungal agent art, and may be prepared using well-known methods. Examples of the pharmaceutically acceptable salts include, but are not limited to, salts comprising acids such as hydrochloric acid, nitric acid, methanesulfonic acid, or oxalic acid.

In accordance with another embodiment, the present invention pertains to a method for preparing the compound of Chemical Formula 1, or pharmaceutically acceptable salts thereof, comprising the reaction of a compound of Chemical Formula 2 with a compound of Chemical Formula 3 in the presence of a base:

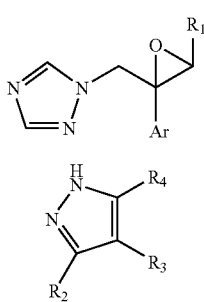

[Chemical Formula 2]

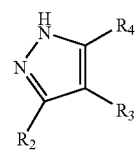

[Chemical Formula 3]

In Chemical Formulas 2 and 3, Ar, $R_1$, $R_2$, $R_3$ and $R_4$ are all as defined above.

As a starting compound for the compound of Chemical Formula 2, an epoxide is well known, and can be prepared, for example, using the method described in the literature [Chem. Pharm. Bull. Tasaka et al., 1993, 41(6), 1035-1042]. The compound of Chemical Formula 3 is commercially available, or may be prepared according to a conventional method well known in the art, for example, disclosed in Chemical Review, Miyaura & Suzuki, 1995, 95, 2457-2483. The preparation of the compound of Chemical Formula 1 through the reaction of the compound of Chemical Formula 2 with the compound of Chemical Formula 3 can be represented by the following reaction formula 1. In this reaction formula, the protecting group (Pr) for NH of the pyrazole may be preferably benzyl, para-methoxybenzyl, trityl, methoxymethyl, 2-methoxyethoxymethyl, 2-(trimethylsilyl)ethoxymethyl, tetrahydropyranyl, or 1-ethoxyethyl.

A base useful in the present invention may be an inorganic base such as sodium hydride, (NaH), potassium carbonate ($K_2CO_3$) or sodium methoxide ($NaOCH_3$), or an organic base such as triethylamine or 1,8-diazabicyclo[5,4,0]undec-7-ene (DBU).

The compound, represented by Chemical Formula 1, of the present invention may be synthesized at 0 to 200° C. using a conventional method or a microwave reactor. Preferably, the preparation reaction of the compound is performed at 30 to 200° C. for 2 min to 24 hours with stirring.

In accordance with a further embodiment, the present invention provides an antifungal composition comprising the compound of Chemical Formula 1 or a pharmaceutical salt thereof as an active ingredient.

The pharmaceutical composition of the present invention can be formulated with the compound of the present invention or a pharmaceutically acceptable salt thereof in combination with an inert pharmaceutical vehicle or a diluent suitable for oral, non-oral or topical administration into various dosage forms using conventional methods.

As injections, which are representative of non-oral dosage forms, isotonic aqueous solutions or suspensions are preferred. Oral dosage forms may be exemplified by tablets, capsules, etc. In addition to the active ingredient, these dosage forms may include diluents (e.g., lactose, dextrose, sucrose, mannitol, sorbitol, cellulose and/or glycine), lubricants (e.g., silica, talc, stearic acid or magnesium or calcium salts thereof, and/or polyethylene glycol) alone or in combination. Tablets may comprise a binder such as magnesium aluminum silicate, starch paste, gelatin, tragacanth, methylcellulose, sodium carboxymethylcellulose and/or polyvinylpyrrolidone, and

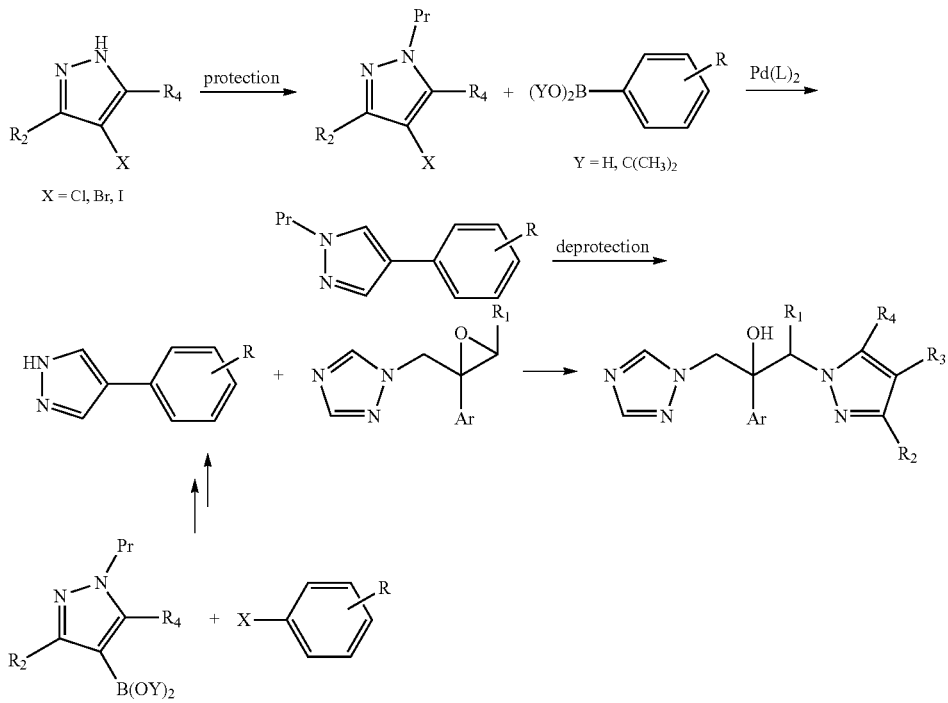

[Reaction Formula 1]

The reaction for the synthesis of the compound according to the present invention may be carried out in a polar organic solvent, which is preferably exemplified by methanol, acetonitrile, dimethoxyethane, dimethylformamide, and dimethylsulfoxide.

optionally disintegrants, such as starch, agar, and alginic acid or sodium salts thereof, boiling mixtures, moisture absorbents, colorants, flavors, and/or sweeteners.

Depending on various factors including conditions of patients, such as severity of disease, sex, etc., administration route, doctor's prescriptions, and the like, the dosage of the active ingredient may vary. A therapeutically effective dose of the compound of the present invention can be readily determined by those who are skilled in the art. For the treatment of mammals infected with fungi, including human beings, for example, the compound of the present invention may be administered in an amount from 0.05 mg/kg/day to 100 mg/kg/day, and preferably in an amount from 1.0 mg/kg/day to 20 mg/kg/day, either orally or via injection routes.

A better understanding of the present invention may be obtained through the following examples which are set forth to illustrate, but are not to be construed as the limit of the present invention.

EXAMPLE 1

(2R,3R)-3-(4-(4-fluorophenyl)-1H-pyrazole-1-yl)-2-(2,4-difluorophenyl)-1-(1H-1,2,4-triazole-1-yl)butane-2-ol Step 1) Synthesis of 4-bromo-1-trityl-1H-pyrazole A suspension of 4-bromo-1H-pyrazole (10 g) in tetrahydrofuran (230 ml) was stirred for 1 hr at room temperature. While argon gas was provided, sodium hydride was slowly added at 0° C. to the suspension, followed by stirring for 30 min and then for an additional 30 min at room temperature. Then, trityl chloride (22.8 g) was slowly added at 0° C. to the suspension with stirring for 20 min. Further stirring was conducted for 3 hrs at room temperature before the reaction was terminated. Following the removal of excess sodium hydride with distilled water (3 ml) from the reaction at 0° C., the tetrahydrofuran solvent was evaporated in a vacuum and the concentrate thus obtained was diluted in ethyl acetate (200 ml) and washed with distilled water (200 ml) and then with brine (200 ml). The resulting organic layer was dried over anhydrous magnesium sulfate and concentrated by evaporation in vacuo. The residue was diluted in methylene chloride (2 ml) and recrystallized in methanol (200 ml) to give 4-bromo-1-trityl-1H-pyrazole (25 g).

$^1$H-NMR (300 MHz, CDCl$_3$): δ7.64 (s, 1H), 7.40 (s, 1H), 7.35-7.33 (m, 9H), 7.17-7.13 (m, 6H).

Step 2) Synthesis of 4-(4-fluorophenyl)-1-trityl-1H-pyrazole

To a suspension of 4-bromo-trityl-1H-pyrazole (0.7 g) in N,N-dimethylformamide (14 ml) was added 4-fluorophenylboronic acid (0.377 g), cesium carbonate (1.758 g), and tetrakis triphenylphosphine palladium (0.208 g). The resulting suspension was stirred at room temperature for 10 min. The irradiation of microwaves at 160° C. for 10 min was sufficient to complete a reaction in the suspension. The product was filtered through silica gel, diluted in ethyl acetate (30 ml) and washed with saturated ammonium chloride solution (30 ml) and then with brine (30 ml). The washed organic layer thus formed was dried over anhydrous magnesium sulfate and concentrated by evaporation in a vacuum. The residue thus obtained was separated using silica gel chromatography to produce 4-(4-fluorophenyl)-1-trityl-1H-pyrazole (yield 51%).

$^1$H-NMR (300 MHz, CDCl$_3$): δ7.93 (s, 1H), 7.62 (s, 1H), 7.36-7.29 (m, 11H), 7.21-7.18 (m, 6H).

Step 3) Synthesis of 4-(4-fluorophenyl)-1H-pyrazole

A suspension of 4-(4-fluorophenyl)-1-trityl-1H-pyrazole (0.370 g) was suspended in a mixture solution of trifluoroacetic acid (5 ml)/methylene chloride (10 ml) and stirred for 10 min at room temperature, followed by irradiating microwaves thereto at 70° C. for 20 min to induce a reaction. After the reaction was terminated, the solution was diluted in methylene chloride (20 ml), neutralized with 1N sodium hydroxide (20 ml), and washed with distilled water (30 ml) and then with brine (20 ml). The washed organic layer thus formed was dried over anhydrous magnesium sulfate and concentrated by evaporation in a vacuum. The residue thus obtained was separated using silica gel chromatography to give 4-(4-fluorophenyl)-1H-pyrazole (Yield 81%).

$^1$H-NMR (300 MHz, CDCl$_3$) δ7.83 (s, 2H), 7.51-7.46 (m, 2H), 7.12-7.07 (m, 2H)

Step 4) Synthesis of (2R,3R)-3-(4-(4-fluorophenyl)-1H-pyrazole-1-yl)-2-(2,4-difluorophenyl)-1-(1H-1,2,4-triazole-1-yl)butane-2-ol To a suspension of 4-(4-fluorophenyl)-1H-pyrazole (0.12 g) in N,N-dimethylformamide (5 ml) were added calcium carbonate (0.15 g) and 1-(((2R,3S)-2-(2,4-difluorophenyl)-3-methyloxiran-2-yl)methyl)-1H-1,2,4-triazole (0.204 g). While argon gas was provided, stirring was conducted at room temperature for 20 min prior to the irradiation of microwaves thereto at 180° C. for 15 min for reaction. After the reaction was terminated, the solution was diluted in ethyl acetate (10 ml) and washed with a saturated ammonium chloride solution (10 ml) and then with brine (10 ml). The washed organic layer thus formed was dried over anhydrous magnesium sulfate and concentrated by evaporation in a vacuum. The residue was separated through silica gel chromatography to give the title compound (Yield 56%).

$^1$H NMR (300 MHz, CDCl3): δ 7.91 (s, 1H), 7.83 (s, 1H), 7.81 (s, 1H), 7.66 (s, 1H), 7.51-7.45 (m, 3H), 7.11-7.05 (m, 2H), 6.80-6.77 (m, 2H), 5.78 (s, 1H), 5.07 (q, 1H), 4.88 (d, 1H), 3.66 (d, 1H), 1.36 (d, 3H).

EXAMPLES 2 TO 56

Compounds 2 to 56, represented by the following Chemical Formula 4,

[Chemical Formula 4]

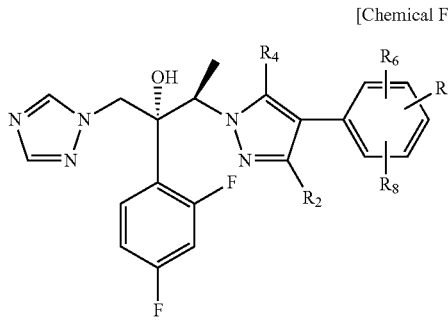

which corresponds to Chemical Formula 1 wherein R$_2$ and R$_4$ are hydrogen and R$_3$ is

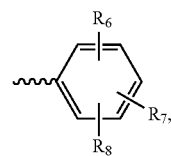

were prepared in a manner similar to that of Example 1. Substituents used for the compounds are summarized in Table 1, below.

[TABLE 1]

| EXAMPLES | R₃ | R₄ | R₆ | R₇ | R₈ | ¹H-NMR (300 MHz, CDCl₃) δ |
|---|---|---|---|---|---|---|
| 2 | H | H | H | H | H | 8.21 (s, 1H), 7.96-7.86 (m, 3H), 7.67 (s, 1H), 7.55-7.51 (m, 3H), 7.42-7.37 (m, 2H), 7.29-7.26 (m, 1H), 6.81-6.77 (m, 2H), 5.08 (q, 1H), 4.88 (d, 1H), 3.70 (d, 1H), 1.37 (d, 3H). |
| 3 | H | H | 2-F | H | H | 8.10 (s, 1H), 7.98 (s, 1H), 7.88 (s, 1H), 7.66 (s, 1H), 7.59-7.49 (m, 2H), 7.22-7.14 (m, 3H), 6.82-6.77 (m, 2H), 5.10 (q, 1H), 4.89 (d, 1H), 3.69 (d, 1H), 1.40 (d, 3H). |
| 4 | H | H | 2-Cl | H | H | 8.13 (s, 1H), 8.01 (s, 1H), 7.90 (s, 1H), 7.67 (s, 1H), 7.59-7.45 (m, 2H), 7.39-7.29 (m, 3H), 6.85-6.77 (m, 2H), 5.18 (q, 1H), 4.95 (d, 1H), 3.73 (d, 1H), 1.41 (d, 3H). |
| 5 | H | H | 2-Br | H | H | 8.17 (s, 1H), 7.96 (s, 1H), 7.88 (s, 1H), 7.66 (s, 1H), 7.52-7.45 (m, 2H), 7.40-7.31 (m, 3H), 6.82-6.77 (m, 2H), 5.10 (q, 1H), 4.89 (d, 1H), 3.69 (d, 1H), 1.40 (d, 3H). |
| 6 | H | H | 2-CN | H | H | 8.15-8.11 (m, 4H), 7.66-7.57 (m, 3H), 7.40 (t, 1H), 7.15 (d, 1H), 6.67-6.61 (m, 2H), 5.09 (q, 2H), 4.87 (d, 1H), 3.71 (d, 1H), 1.39 (d, 3H). |
| 7 | H | H | 2-NO₂ | H | H | 8.35 (s, 1H), 8.25-8.23 (m, 2H), 8.15 (s, 1H), 8.11 (s, 1H), 7.74-7.71 (m, 2H), 7.48 (t, 1H), 7.15 (d, 1H), 6.67-6.61 (m, 2H), 5.11 (q, 1H), 4.86 (d, 1H), 3.72 (d, 1H), 1.41 (d, 3H). |
| 8 | H | H | 3-F | H | H | 7.97 (s, 1H), 7.90 (s, 1H), 7.86 (s, 1H), 7.69 (s, 1H), 7.51 (m, 1H), 7.36-7.31 (m, 3H), 7.24-7.20 (m, 1H), 6.80-6.78 (m, 2H), 5.09 (q, 1H), 4.90 (d, 1H), 3.39 (d, 1H), 1.37 (d, 3H). |
| 9 | H | H | 3-Cl | H | H | 8.01 (s, 1H), 7.93 (s, 1H), 7.88 (s, 1H), 7.70 (s, 1H), 7.51 (m, 1H), 7.40-7.35 (m, 4H), 6.80-6.78 (m, 2H), 5.12 (q, 1H), 4.94 (d, 1H), 3.41 (d, 1H), 1.38 (d, 3H). |
| 10 | H | H | 3-Br | H | H | 7.97-7.66 (m, 5H), 7.50-7.21 (m, 4H), 6.81-6.76 (m, 2H), 5.84 (bs, 1H), 5.07 (q, 1H), 4.88 (d, 1H), 3.68 (d, 1H), 1.36 (d, 3H). |
| 11 | H | H | 3-CF₃ | H | H | 8.35 (s, 1H), 8.23 (s, 1H), 8.15 (s, 1H), 8.11 (s, 1H), 7.67 (s, 1H), 7.48 (d, 1H), 7.41 (d, 1H), 7.25 (t, 1H), 7.15 (d, 1H), 6.67-6.61 (m, 2H), 4.32 (q, 1H), 4.30 (d, 1H), 4.05 (d, 1H), 1.61 (d, 3H). |
| 12 | H | H | 3-CN | H | H | 8.15-7.97 (m, 4H), 7.76-7.73 (m, 2H), 7.75-7.47 (m, 2H), 7.15 (d, 1H), 6.67-6.61 (m, 2H), 5.06 (q, 1H), 4.87 (d, 1H), 3.70 (d, 1H), 1.40 (d, 3H). |
| 13 | H | H | 3-NO₂ | H | H | 8.41 (s, 1H), 8.35-8.23 (m, 2H), 8.15-8.11 (m, 3H), 7.87 (d, 1H), 7.58 (t, 1H), 7.15 (d, 1H), 6.67-6.61 (m, 2H), 5.08 (q, 1H), 4.88 (d, 1H), 3.71 (d, 1H), 1.40 (d, 3H). |
| 14 | H | H | 4-Cl | H | H | 7.94 (s, 1H), 7.86 (s, 1H), 7.84 (s, 1H), 7.68 (s, 1H), 7.52-7.44 (m, 3H), 7.38-7.34 (m, 2H), 6.84-6.77 (m, 2H), 5.80 (bs, 1H), 5.09 (q, 1H), 4.87 (d, 1H), 3.70 (d, 1H), 1.36 (d, 3H). |
| 15 | H | H | 4-Br | H | H | 7.97 (s, 1H), 7.95 (s, 1H), 7.84 (s, 1H), 7.70 (s, 1H), 7.54-7.49 (m, 3H), 7.41-7.37 (m, 2H), 6.84-6.77 (m, 2H), 5.81 (bs, 1H), 5.08 (q, 1H), 4.89 (d, 1H), 3.71 (d, 1H), 1.36 (d, 3H). |
| 16 | H | H | 4-OCH₃ | H | H | 7.97 (s, 1H), 7.82 (m, 2H), 7.69 (s, 1H), 7.67-7.60 (m, 4H), 7.55-7.47 (m, 1H), 6.85-6.78 (m, 2H), 5.05 (q, 1H), 4.88 (d, 1H), 3.73 (d, 1H), 1.64 (d, 3H), 1.35 (d, 3H). |
| 17 | H | H | 4-NO₂ | H | H | 8.28-8.24 (m, 2H), 8.12 (d, 1H), 7.94 (s, 1H), 7.87 (d, 1H), 7.71-7.65 (m, 3H), 7.52-7.50 (m, 1H), 6.84-6.78 (m, 2H), 5.62 (bs, 1H), 5.14 (q, 1H), 4.93 (d, 1H), 3.73 (d, 1H), 1.24 (d, 3H). |
| 18 | H | H | 4-CF₃ | H | H | 8.04 (s, 1H), 7.93-7.90 (m, 2H), 7.70 (s, 1H) 7.67-7.60 (m, 4H), 7.55-7.47 (m, 1H), 6.85-6.78 (m, 2H), 5.11 (q, 1H), 4.92 (d, 1H), 3.72 (d, 1H), 1.41 (d, 3H). |
| 19 | H | H | 4-CN | H | H | 7.99 (s, 1H), 7.84 (d, 2H), 7.68 (s, 1H), 7.36-7.29 (m, 4H), 7.23 (s, 1H), 6.84-6.78 (m, 2H), 5.75 (s, 1H), 5.09 (q, 1H), 4.89 (d, 1H), 3.69 (d, 1H), 1.37 (d, 3H). |
| 20 | H | H | 4-OCF₃ | H | H | 7.96 (s, 1H), 7.84 (d, 2H), 7.68 (s, 1H), 7.56-7.49 (m, 4H), 7.23 (s, 1H), 6.84-6.78 (m, 2H), 5.75 (s, 1H), 5.09 (q, 1H), 4.89 (d, 1H), 3.69 (d, 1H), 1.37 (d, 3H). |

[TABLE 1]-continued

| EXAMPLES | R₃ | R₄ | R₅ | | | ¹H-NMR (300 MHz, CDCl₃) δ |
|---|---|---|---|---|---|---|
| | | | R₆ | R₇ | R₈ | |
| 21 | H | H | 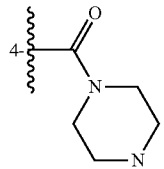 | H | H | 8.01 (s, 1H), 7.88 (s, 1H), 7.83 (s, 1H), 7.68 (s, 1H), 7.57 (d, 2H), 7.45 (d, 2H), 6.80 (t, 2H), 5.74 (s, 1H), 5.09 (q, 1H), 4.88 (d, 1H), 3.72-3.67 (m, 9H), 1.37 (d, 3H). |
| 22 | H | H | 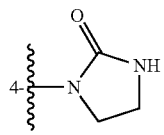 | H | H | 7.84 (s, 1H), 7.78 (d, 2H), 7.59 (s, 1H), 7.53 (s, 1H), 7.51 (s, 1H), 7.45-7.41 (m, 3H), 6.73-6.70 (m, 2H), 5.80 (s, 1H), 5.00 (q, 1H), 4.81 (d, 1H), 3.94-3.89 (m, 2H), 3.64 (d, 1H), 3.56-3.51 (m, 2H), 1.30 (d, 3H). |
| 23 | H | H | 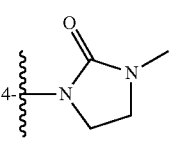 | H | H | 7.84 (s, 1H), 7.78 (d, 2H), 7.59 (s, 1H), 7.53 (s, 1H), 7.51 (s, 1H), 7.45-7.41 (m, 3H), 6.73-6.70 (m, 2H), 5.80 (s, 1H), 5.00 (q, 1H), 4.81 (d, 1H), 3.78-3.72 (m, 2H), 3.64 (d, 1H), 3.43-3.38 (m, 2H), 1.30 (d, 3H). |
| 24 | H | H | 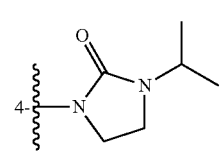 | H | H | 7.84 (s, 1H), 7.78 (d, 2H), 7.59 (s, 1H), 7.53 (s, 1H), 7.51 (s, 1H), 7.45-7.41 (m, 3H), 6.73-6.70 (m, 2H), 5.80 (s, 1H), 5.00 (q, 1H), 4.81 (d, 1H), 4.23-4.19 (m, 1H), 3.79-3.73 (m, 2H), 3.63 (d, 1H), 3.42-3.36 (m, 2H), 1.29 (d, 3H), 1.13 (d, 6H). |
| 25 | H | H | 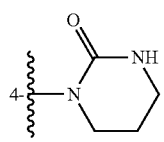 | H | H | 7.90 (s, 1H), 7.85-7.82 (d, 2H), 7.64 (s, 1H), 7.47 (d, 3H), 7.32 (d, 2H), 6.83-6.75 (m, 2H), 5.05 (q, 1H), 4.86 (d, 1H), 3.71-3.66 (m, 2H), 3.41 (d, 3H), 2.12-2.03 (m, 2H) 1.34 (d, 3H). |
| 26 | H | H | 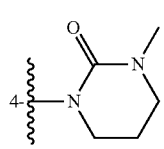 | H | H | 8.02 (d, 2H), 7.82 (s, 1H), 7.69 (s, 1H), 7.63 (s, 1H), 7.41 (d, 2H), 7.27 (s, 1H), 7.00-6.98 (m, 1H), 6.87-6.78 (m, 2H), 4.99-4.90 (q, 1H), 3.71 (t, 2H), 3.41-3.37 (m, 3H), 3.00 (s, 3H), 2.17-2.11 (m, 2H), 1.28-1.25 (d, 3H). |
| 27 | H | H | 3-F | 5-F | H | 7.92 (s, 1H), 7.76 (s, 2H), 7.62 (s, 1H), 7.45-7.42 (q, 1H), 6.98-6.94 (m, 2H), 6.77-6.70 (m, 2H), 6.66-6.60 (m, 1H), 5.03 (q, 1H), 4.83 (d, 1H), 3.62 (d, 1H), 1.30 (d, 3H). |
| 28 | H | H | 3-Cl | 5-F | H | 8.05 (s, 1H), 7.99 (s, 1H), 7.88 (s, 1H), 7.65 (s, 1H), 7.36-7.27 (m, 3H), 6.94 (s, 1H), 6.67-6.61 (m, 2H), 5.81 (bs, 1H), 5.11 (q, 1H), 4.92 1H), 3.72 (d, 1H), 1.41 (d, 3H). |
| 29 | H | H | 3-Cl | 4-CH₃ | 5-F | 8.02 (s, 1H), 7.98 (s, 1H), 7.85 (s, 1H), 7.65 (s, 1H), 7.34-7.26 (m, 2H), 6.95 (s, 1H), 6.67-6.61 (m, 2H), 5.82 (bs, 1H), 5.10 (q, 1H), 4.91 (d, 1H), 3.71 (d, 1H), 2.35 (s, 3H), 1.40 (d, 3H). |
| 30 | H | H | 2-F | 4-F | H | 8.07 (s, 1H), 7.93 (s, 1H), 7.84 (s, 1H), 7.69 (s, 1H), 7.57-7.52 (m, 2H), 6.98-6.93 (m, 2H), 6.82-6.79 (m, 2H), 5.80 (s, 1H), 5.12 (q, 1H), 4.91 (d, 1H), 3.70 (d, 1H), 1.42 (d, 3H). |
| 31 | H | H | 3-CH₃ | 4-F | H | 7.85 (d, 2H), 7.75 (s, 1H), 7.63 (s, 1H), 7.44 (q, 1H), 7.28-7.19 (m, 2H), 6.96 (t, 1H), 6.78-6.71 (m, 2H), 5.01 (q, 1H), 4.83 (d, 1H), 3.63 (d, 1H), 2.25 (s, 3H), 1.30 (d, 3H). |
| 32 | H | H | 2-CH₃ | 4-F | H | 7.81 (s, 1H), 7.69 (s, 1H), 7.61 (s, 2H), 7.45 (d, 1H), 7.25-7.20 (m, 1H), 6.93-6.86 (m, 2H), 6.77-6.71 (m, 2H), 5.02 (q, 1H), 4.79 (d, 1H), 3.63 (d, 1H), 2.33 (s, 3H), 1.31 (d, 3H). |
| 33 | H | H | 2-OCH₃ | 4-F | H | 7.91 (s, 1H), 7.75 (s, 1H), 7.67 (s, 2H), 7.48 (d, 1H), 7.28-7.21 (m, 1H), 6.93-6.85 (m, 2H), 6.76-6.70 (m, 2H), 5.01 (q, 1H), 4.81 (d, 1H), 3.64 (d, 1H), 2.97 (s, 3H), 1.32 (d, 3H). |

[TABLE 1]-continued

| EXAMPLES | R₃ | R₄ | R₆ | R₇ | R₈ | ¹H-NMR (300 MHz, CDCl₃) δ |
|---|---|---|---|---|---|---|
| 34 | H | H | 3-OCH₃ | 4-F | H | 7.90 (s, 1H), 7.75 (s, 1H), 7.65 (s, 2H), 7.49 (d, 1H), 7.27-7.21 (m, 1H), 6.92-6.85 (m, 2H), 6.76-6.70 (m, 2H), 5.01 (q, 1H), 4.81 (d, 1H), 3.64 (d, 1H), 2.98 (s, 3H), 1.33 (d, 3H). |
| 35 | H | H | 3-Cl | 4-F | H | 8.04 (s, 1H), 7.98 (s, 1H), 7.89 (s, 1H), 7.63 (s, 1H), 7.38-7.27 (m, 3H), 6.94 (s, 1H), 6.67-6.61 (m, 2H), 5.82 (bs, 1H), 5.09 (q, 1H), 4.92 (d, 1H), 3.72 (d, 1H), 1.40 (d, 3H). |
| 36 | H | H | 2-F | 4-Cl | H | 8.05 (s, 1H), 7.86 (s, 1H), 7.77 (s, 1H), 7.60 (s, 1H), 7.47-7.41 (m, 2H), 7.13-7.09 (m, 2H), 6.74-6.70 (q, 2H), 5.07-5.00 (q, 1H), 4.82 (d, 1H), 3.62 (d, 1H), 1.30 (d, 3H). |
| 37 | H | H | 3-Cl | 4-Cl | H | 8.07 (s, 1H), 8.00 (s, 1H), 7.91 (s, 1H), 7.63 (s, 1H), 7.38-7.27 (m, 3H), 6.94 (s, 1H), 6.67-6.61 (m, 2H), 5.82 (bs, 1H), 5.09 (q, 1H), 4.92 (d, 1H), 3.72 (d, 1H), 1.35 (d, 3H). |
| 38 | H | H | 2-CH₃ | 4-Cl | H | 7.83 (s, 1H), 7.71 (s, 1H), 7.63 (s, 2H), 7.47 (d, 1H), 7.25-7.20 (m, 1H), 6.94-6.86 (m, 2H), 6.77-6.71 (m, 2H), 5.01 (q, 1H), 4.79 (d, 1H), 3.63 (d, 1H), 2.33 (s, 3H), 1.32 (d, 3H). |
| 39 | H | H | 3-CH₃ | 4-Cl | H | 7.87 (d, 2H), 7.76 (s, 1H), 7.65 (s, 1H), 7.44 (q, 1H), 7.28-7.19 (m, 2H), 6.97 (t, 1H), 6.78-6.71 (m, 2H) 5.01 (q, 1H), 4.84 (d, 1H), 3.63 (d, 1H), 2.27 (s, 3H), 1.32 (d, 3H). |
| 40 | H | H | 2-OCH₃ | 4-Cl | H | 7.93 (s, 1H), 7.77 (s, 1H), 7.68 (s, 2H), 7.49 (d, 1H), 7.28-7.21 (m, 1H), 6.94-6.85 (m, 2H), 6.76-6.70 (m, 2H), 5.02 (q, 1H), 4.81 (d, 1H), 3.64 (d, 1H), 2.96 (s, 3H), 1.31 (d, 3H). |
| 41 | H | H | 3-CN | 4-Cl | H | 8.05 (s, 1H), 8.00 (s, 1H), 7.95 (s, 1H), 7.57 (s, 1H), 7.27-7.27 (m, 1H), 7.11-7.05 (m, 2H), 6.67-6.61 (m, 2H), 5.06 (q, 1H), 4.82 (d, 1H), 3.65 (d, 1H), 1.36 (d, 3H). |
| 42 | H | H | 3-NO₂ | 4-Cl | H | 8.25 (s, 1H), 8.11 (s, 1H), 7.95 (s, 1H), 7.67 (s, 1H), 7.38-7.29 (m, 2H), 7.11-7.05 (m, 2H), 6.68-6.61 (m, 2H), 5.05 (q, 1H), 4.81 (d, 1H), 3.66 (d, 1H), 1.35 (d, 3H). |
| 43 | H | H | 3-Cl | 5-Cl | H | 8.02 (s, 1H), 7.85 (s, 1H), 7.72 (s, 1H), 7.51 (q, 1H), 7.41 (s, 1H), 7.26 (d, 1H) 6.83 (t, 2H), 5.11 (q, 1H), 4.92 (d, 1H), 3.69 (d, 1H), 1.39 (d, 3H). |
| 44 | H | H | 3-F | 4-CN | H | 8.04 (s, 1H), 7.99 (s, 1H), 7.94 (s, 1H), 7.58 (s, 1H), 7.35-7.28 (m, 2H), 7.10-7.05 (m, 2H), 6.69-6.61 (m, 2H), 5.06 (q, 1H), 4.81 (d, 1H), 3.66 (d, 1H), 1.36 (d, 3H). |
| 45 | H | H | 4-Morpholine | H | H | 8.35 (s, 1H), 8.23 (s, 1H), 8.15 (s, 1H), 8.11 (s, 1H), 7.30 (dd, 2H), 7.15 (d, 1H), 6.67-6.61 (m, 4H), 4.32 (q, 1H), 4.30 (d, 1H), 4.05 (d, 1H), 3.67 (m, 4H), 2.90 (m, 4H), 1.61 (d, 3H). |
| 46 | H | H | 3-Morpholine | H | H | 8.35 (s, 1H), 8.23 (s, 1H), 8.15 (s, 1H), 8.11 (s, 1H), 7.15-7.14 (m, 2H), 6.82-6.81 (m, 2H), 6.67-6.55 (m, 3H), 4.32 (q, 1H), 4.30 (d, 1H), 4.05 (d, 1H), 3.67 (m, 4H), 2.90 (m, 4H), 1.61 (d, 3H). |
| 47 | H | H | 2-Morpholine | H | H | 8.35 (s, 1H), 8.23 (s, 1H), 8.15 (s, 1H), 8.11 (s, 1H), 7.30 (d, 1H), 7.15 (d, 1H), 7.04 (t, 1H), 6.67-6.61 (m, 4H), 4.32 (q, 1H), 4.30 (d, 1H), 4.05 (d, 1H), 3.67 (m, 4H), 2.90 (m, 4H), 1.61 (d, 3H). |
| 48 | H | H | 3-pyrrolidine | H | H | 8.35 (s, 1H), 8.23 (s, 1H), 8.15 (s, 1H), 8.11 (s, 1H), 7.15-7.14 (m, 2H), 6.82-6.81 (m, 2H), 6.67-6.55 (m, 3H), 4.32 (q, 1H), 4.30 (d, 1H), 4.05 (d, 1H), 2.80 (m, 4H), 1.61 (d, 3H), 1.59 (m, 4H). |
| 49 | CH₃ | H | 2-Cl | H | H | 7.92 (s, 1H), 7.74 (s, 1H), 7.66 (s, 1H), 7.50-7.47 (m, 2H), 7.34-7.27 (m, 3H), 6.79-6.77 (m, 2H), 4.99 (q, 1H), 4.86 (d, 1H), 3.78 (d, 1H), 2.29 (s, 3H), 1.34 (d, 3H). |
| 50 | CH₃ | H | 2-Br | H | H | 7.94 (s, 1H), 7.80 (s, 1H), 7.68 (s, 1H), 7.53-7.50 (m, 2H), 7.37-7.30 (m, 3H), 6.81-6.79 (m, 2H), 5.01 (q, 1H), 4.88 (d, 1H), 3.80 (d, 1H), 2.31 (s, 3H), 1.36 (d, 3H). |

[TABLE 1]-continued

| EXAMPLES | $R_3$ | $R_4$ | $R_5$ / $R_6$ | $R_7$ | $R_8$ | $^1$H-NMR (300 MHz, CDCl$_3$) δ |
|---|---|---|---|---|---|---|
| 51 | CH$_3$ | H | 3-F | H | H | 8.02 (s, 1H), 7.72 (s, 1H), 7.60 (s, 1H), 7.56-7.53 (m, 1H), 7.40-7.38 (m, 1H), 7.17-7.14 (m, 1H), 7.10-7.02 (m, 2H), 6.83-6.80 (m, 2H), 5.11 (q, 1H), 4.73 (d, 1H), 3.74 (d, 1H), 2.51 (s, 3H), 1.29 (d, 3H). |
| 52 | CH$_3$ | H | 3-Cl | H | H | 8.16 (s, 1H), 7.89 (s, 1H), 7.72 (s, 1H), 7.49-7.36 (m, 2H), 7.26-7.15 (m, 3H), 6.67-6.61 (m, 2H), 5.10 (q, 1H), 4.74 (d, 1H), 3.75 (d, 1H), 2.51 (s, 3H), 1.30 (d, 3H). |
| 53 | CH$_3$ | H | 3-CF$_3$ | H | H | 8.22 (s, 1H), 7.95 (s, 1H), 7.79 (s, 1H), 7.55-7.41 (m, 2H), 7.29-7.15 (m, 3H), 6.67-6.61 (m, 2H), 5.11 (q, 1H), 4.73 (d, 1H), 3.74 (d, 1H), 2.51 (s, 3H), 1.30 (d, 3H). |
| 54 | H | CH$_3$ | 3-F | H | H | 7.96 (s, 1H), 7.82 (s, 1H), 7.76 (s, 1H), 7.38-7.32 (m, 1H), 7.20-6.99 (m, 4H), 6.81-6.71 (m, 2H), 4.88 (q, 1H), 4.43 (d, 1H), 3.19 (d, 1H), 2.52 (s, 3H), 1.64 (d, 3H). |
| 55 | H | CH$_3$ | 3-Cl | H | H | 8.18 (s, 1H), 7.95 (s, 1H), 7.85 (s, 1H), 7.37-7.33 (m, 1H), 7.21-7.00 (m, 4H), 6.82-6.73 (m, 2H), 4.89 (q, 1H), 4.45 (d, 1H), 3.21 (d, 1H), 2.52 (s, 3H), 1.61 (d, 3H). |
| 56 | 4-Py | H | 4-CF$_3$ | H | H | 8.57 (d, 2H), 8.11 (s, 1H), 7.96 (s, 1H), 7.81 (s, 1H), 7.69-7.61 (m, 2H), 7.39 (d, 2H), 7.01-6.99 (m, 2H), 6.85-6.72 (m, 2H), 4.85 (q, 1H), 4.43 (d, 1H), 3.25 (d, 1H), 1.52 (d, 3H). |

EXAMPLES 57 TO 82

Compounds 57 to 82, represented by the following Chemical Formula 5,

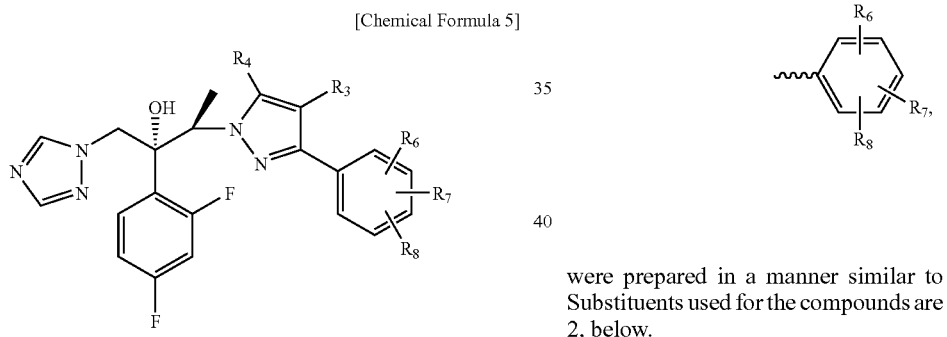

[Chemical Formula 5]

which corresponds to Chemical Formula 1 wherein $R_3$ and $R_4$ are hydrogen and $R_2$ is were prepared in a manner similar to that of Example 1. Substituents used for the compounds are summarized in Table 2, below.

TABLE 2

| EXAMPLES | $R_3$ | $R_4$ | $R_2$ / $R_6$ | $R_7$ | $R_8$ | $^1$H-NMR (300 MHz, CDCl$_3$) δ |
|---|---|---|---|---|---|---|
| 57 | H | H | H | H | H | 7.87 (d, 3H), 7.73 (s, 1H), 7.65 (s, 1H), 7.54 (m, 3H), 7.37 (t, 1H), 6.83-6.78 (q, 2H), 6.68 (s, 1H), 5.09 (q, 1H), 4.85 (d, 1H), 3.73 (d, 1H), 1.39 (d, 3H). |
| 58 | H | H | 2-F | H | H | 7.82 (s, 1H), 7.69 (s, 1H), 7.71-7.62 (m, 3H), 7.50-7.41 (m, 2H), 7.28 (m, 1H), 6.79-6.72 (m, 3H), 5.07 (q, 1H), 4.87 (d, 1H), 3.72 (d, 1H), 1.37 (d, 3H). |
| 59 | H | H | 2-Cl | H | H | 7.85 (s, 1H), 7.71 (s, 1H), 7.65-7.60 (m, 3H), 7.49-7.39 (m, 2H), 7.24 (m, 1H), 6.80-6.74 (m, 3H), 5.11 (q, 1H), 4.87 (d, 1H), 3.72 (d, 1H), 1.38 (d, 3H). |
| 60 | H | H | 2-Br | H | H | 7.90 (s, 1H), 7.74 (s, 1H), 7.70-7.63 (m, 3H), 7.51-7.39 (m, 2H), 7.25 (m, 1H), 6.81-6.74 (m, 3H), 5.09 (q, 1H), 4.87 (d, 1H), 3.76 (d, 1H), 1.39 (d, 3H). |
| 61 | H | H | 2-NO$_2$ | H | H | 8.21 (s, 1H), 8.09 (s, 1H), 8.00 (s, 1H), 7.70-7.63 (m, 3H), 7.21-7.18 (m, 1H), 7.05-6.99 (m, 2H), 6.81-6.74 (m, 3H), 5.15 (q, 1H), 4.87 (d, 1H), 3.76 (d, 1H), 1.39 (d, 3H). |

TABLE 2-continued

| EXAMPLES | R₃ | R₄ | R₂ / R₆ | R₇ | R₈ | ¹H-NMR (300 MHz, CDCl₃) δ |
|---|---|---|---|---|---|---|
| 62 | H | H | 2-CF₃ | H | H | 7.90 (s, 1H), 7.74 (s, 1H), 7.70-7.63 (m, 3H), 7.51-7.39 (m, 2H), 7.25 (m, 1H), 6.81-6.74 (m, 3H), 5.09 (q, 1H), 4.87 (d, 1H), 3.76 (d, 1H), 1.39 (d, 3H). |
| 63 | H | H | 3-F | H | H | 7.89 (s, 1H), 7.78 (s, 1H), 7.68 (d, 2H), 7.60 (s, 1H), 7.48-7.42 (m, 2H), 7.21 (t, 1H), 6.80-6.78 (m, 2H), 6.61 (s, 1H), 5.08 (q, 1H), 4.86 (d, 1H), 3.72 (d, 1H), 1.38 (d, 3H). |
| 64 | H | H | 3-Cl | H | H | 7.96 (s, 1H), 7.87 (s, 1H), 7.70 (d, 2H), 7.61 (s, 1H), 7.49-7.42 (m, 2H), 7.29 (t, 1H), 6.80-6.78 (m, 2H), 6.65 (s, 1H), 5.11 (q, 1H), 4.85 (d, 1H), 3.71 (d, 1H), 1.38 (d, 3H). |
| 65 | H | H | 3-Br | H | H | 8.01 (s, 1H), 7.85 (s, 1H), 7.74 (d, 2H), 7.66 (s, 1H), 7.50-7.46 (m, 2H), 7.30 (t, 1H), 6.81-6.78 (m, 2H), 6.65 (s, 1H), 5.09 (q, 1H), 4.86 (d, 1H), 3.70 (d, 1H), 1.38 (d, 3H). |
| 66 | H | H | 3-NO₂ | H | H | 8.25 (s, 1H), 8.12 (s, 1H), 8.04 (s, 1H), 7.81 (d, 1H), 7.74-7.65 (m, 1H), 7.53-7.45 (m, 1H), 7.17-7.12 (m, 1H), 7.00-6.92 (m, 2H), 6.78-6.75 (m, 2H), 5.19 (m, 1H), 4.91 (d, 1H), 3.42 (d, 1H), 1.38 (d, 3H). |
| 67 | H | H | 3-CF₃ | H | H | 7.91 (s, 1H), 7.75 (s, 1H), 7.62 (d, 2H), 7.58 (s, 1H), 7.48-7.41 (m, 2H), 7.25 (m, 1H), 6.81-6.79 (m, 2H), 6.61 (s, 1H), 5.09 (q, 1H), 4.84 (d, 1H), 3.72 (d, 1H), 1.38 (d, 3H). |
| 68 | H | H | 4-F | H | H | 7.71 (s, 1H), 7.59 (s, 1H), 7.50-7.41 (m, 3H), 7.30-7.20 (m, 3H), 6.81-6.77 (m, 2H), 6.60 (s, 1H), 5.08 (q, 1H), 4.84 (d, 1H), 3.71 (d, 1H), 1.38 (d, 3H). |
| 69 | H | H | 4-Cl | H | H | 7.79 (s, 1H), 7.60 (s, 1H), 7.51-7.42 (m, 3H), 7.31-7.25 (m, 3H), 6.83-6.77 (m, 2H), 6.64 (s, 1H), 5.08 (q, 1H), 4.85 (d, 1H), 3.72 (d, 1H), 1.38 (d, 3H). |
| 70 | H | H | 4-Br | H | H | 7.84 (s, 1H), 7.66 (s, 1H), 7.57-7.50 (m, 3H), 7.34-7.27 (m, 3H), 6.84-6.77 (m, 2H), 6.64 (s, 1H), 5.08 (q, 1H), 4.85 (d, 1H), 3.71 (d, 1H), 1.37 (d, 3H). |
| 71 | H | H | 4-NO₂ | H | H | 8.20 (s, 1H), 8.10 (s, 1H), 8.02 (s, 1H), 7.80 (d, 1H), 7.75-7.65 (m, 1H), 7.55-7.45 (m, 1H), 7.16-7.13 (m, 1H), 7.00-6.93 (m, 2H), 6.79-6.78 (m, 2H), 5.20 (m, 1H), 4.90 (d, 1H), 3.45 (d, 1H), 1.39 (d, 3H). |
| 72 | H | H | 4-CF₃ | H | H | 7.90 (s, 1H), 7.72 (s, 1H), 7.60 (d, 2H), 7.54 (s, 1H), 7.48-7.41 (m, 2H), 7.20 (m, 1H), 6.85-6.79 (m, 2H), 6.61 (s, 1H), 5.09 (q, 1H), 4.85 (d, 1H), 3.71 (d, 1H), 1.38 (d, 3H). |
| 73 | H | H | 4-OCF₃ | H | H | 7.87 (q, 3H), 7.75 (s, 1H), 7.68 (s, 1H), 7.52 (q, 1H), 7.31 (s, 2H), 6.85-6.78 (m, 2H), 6.66 (s, 1H), 5.11 (q, 1H), 4.87 (d, 1H), 3.72 (d, 1H), 1.27 (d, 3H). |
| 74 | H | H | 4-CN | H | H | 7.95 (d, 2H), 7.80 (t, 2H), 7.73 (s, 1H), 7.78 (d, 2H), 7.51 (q, 1H), 6.81 (t, 2H), 6.72 (s, 1H), 5.13 (q, 1H), 4.88 (d, 1H), 3.71 (d, 1H), 1.38 (d, 3H). |
| 75 | H | H | 2-F | 4-F | H | 7.85 (s, 1H), 7.72 (s, 1H), 7.60 (d, 1H), 7.45-7.35 (m, 3H), 7.16 (m, 1H), 6.68-6.51 (m, 3H), 5.12 (q, 1H), 4.81 (d, 1H), 3.71 (d, 1H), 1.38 (d, 3H). |
| 76 | H | H | 2-F | 6-F | H | 7.83 (s, 1H), 7.71 (s, 1H), 7.59 (d, 1H), 7.41-7.35 (m, 3H), 7.18 (m, 1H), 6.67-6.51 (m, 3H), 5.12 (q, 1H), 4.81 (d, 1H), 3.72 (d, 1H), 1.38 (d, 3H). |
| 77 | H | H | 2-Cl | 4-Cl | H | 7.95 (s, 1H), 7.81 (s, 1H), 7.68 (d, 1H), 7.46-7.35 (m, 3H), 7.15 (m, 1H), 6.67-6.51 (m, 3H), 5.12 (q, 1H), 4.83 (d, 1H), 3.70 (d, 1H), 1.39 (d, 3H). |
| 78 | H | H | 3-Cl | 4-Cl | H | 7.97 (s, 1H), 7.80 (s, 1H), 7.69 (d, 1H), 7.48-7.35 (m, 3H), 7.13 (m, 1H), 6.65-6.51 (m, 3H), 5.12 (q, 1H), 4.83 (d, 1H), 3.71 (d, 1H), 1.40 (d, 3H). |
| 79 | CH₃ | H | 4-F | H | H | 7.79 (s, 1H), 7.64-7.58 (m, 3H), 7.45 (m, 2H), 7.07 (t, 2H), 6.73-6.69 (m, 2H), 4.93 (q, 1H), 4.77 (d, 1H), 3.68 (d, 1H), 2.19 (s, 3H), 1.27 (d, 3H). |
| 80 | CH₃ | H | 4-Cl | H | H | 7.86 (s, 1H), 7.73 (s, 1H), 7.66 (s, 1H), 7.61-7.49 (m, 3H), 7.38-7.34 (m, 2H), 6.79-6.77 (m, 2H), 5.01 (q, 1H), 4.86 (d, 1H), 3.73 (d, 1H), 2.28 (s, 3H), 1.34 (d, 3H). |
| 81 | H | CH₃ | H | H | H | 7.99 (s, 1H), 7.82 (d, 2H), 7.57 (s, 1H), 7.55-7.36 (m, 4H), 6.82-6.80 (m, 2H), 6.46 (s, 1H), 5.06 (q, 1H), 4.74 (d, 1H), 3.71 (d, 1H), 2.47 (d, 3H), 1.32 (d, 3H). |
| 82 | H | CH₃ | 4-Br | H | H | 7.97 (s, 1H), 7.69 (d, 2H), 7.58-7.54 (m, 4H), 6.84-6.79 (m, 2H), 6.44 (s, 1H), 5.07 (q, 1H), 4.73 (d, 1H), 3.73 (d, 1H), 2.74 (s, 3H), 1.32 (d, 3H). |

EXAMPLES 83 TO 92

Compounds 83 to 92, represented by the following Chemical Formula 6,

[Chemical Formula 6]

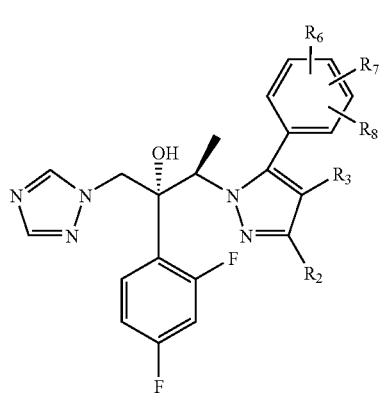

which corresponds to Chemical Formula 1, wherein $R_2$ and $R_3$ are hydrogen and $R_4$ is

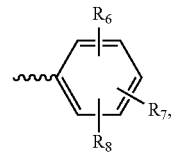

were prepared in a manner similar to that of Example 1. Substituents used for the compounds are summarized in Table 3, below.

TABLE 3

| EXAMPLES | $R_2$ | $R_3$ | $R_4$ $R_6$ | $R_7$ | $R_8$ | $^1$H-NMR (300 MHz, CDCl$_3$) δ |
|---|---|---|---|---|---|---|
| 83 | H | H | H | H | H | 7.64 (s, 1H), 7.50 (s, 1H), 7.42-7.37 (m, 4H), 7.31 (d, 1H), 7.20-7.11 (m, 3H), 6.67-6.62 (m, 2H), 6.50 (d, 1H), 5.07 (q, 1H), 4.86 (d, 1H), 3.69 (d, 1H), 1.37 (d, 3H). |
| 84 | H | H | 2-Br | H | H | 7.91 (s, 1H), 7.75 (s, 1H), 7.69 (d, 2H), 7.49-7.47 (m, 2H), 7.37 (d, 1H), 7.26 (d, 1H), 7.15-7.11 (m, 2H), 6.67-6.61 (m, 2H), 6.51 (d, 1H), 5.09 (q, 1H), 4.87 (d, 1H), 3.69 (d, 1H), 1.38 (d, 3H). |
| 85 | H | H | 3-Br | H | H | 8.00 (s, 1H), 7.86 (s, 1H), 7.74 (d, 2H), 7.66 (s, 1H), 7.52-7.45 (m, 2H), 7.33-7.26 (m, 1H), 6.80-6.77 (m, 2H), 6.65 (s, 1H), 5.10 (q, 1H), 4.86 (d, 1H), 3.70 (d, 1H), 1.37 (d, 3H). |
| 86 | H | H | 4-Br | H | H | 7.84 (s, 1H), 7.70 (s, 1H), 7.66 (d, 2H), 7.45-7.47 (m, 2H), 7.38 (d, 1H), 7.25 (d, 1H), 7.15-7.11 (m, 2H), 6.67-6.62 (m, 2H), 6.50 (d, 1H), 5.07 (q, 1H), 4.86 (d, 1H), 3.69 (d, 1H), 1.37 (d, 3H). |
| 87 | H | H | 4-F | H | H | 7.71 (s, 1H), 7.62 (s, 1H), 7.58 (d, 2H), 7.47-7.47 (m, 2H), 7.32 (d, 1H), 7.21 (d, 1H), 7.16-7.11 (m, 2H), 6.68-6.61 (m, 2H), 6.44 (d, 1H), 5.11 (q, 1H), 4.87 (d, 1H), 3.72 (d, 1H), 1.37 (d, 3H). |
| 88 | H | H | 4-Cl | H | H | 7.75 (s, 1H), 7.66 (s, 1H), 7.61 (d, 2H), 7.46-7.47 (m, 2H), 7.37 (d, 1H), 7.22 (d, 1H), 7.16-7.11 (m, 2H), 6.68-6.62 (m, 2H), 6.49 (d, 1H), 5.09 (q, 1H), 4.87 (d, 1H), 3.71 (d, 1H), 1.38 (d, 3H). |
| 89 | H | H | 2-Cl | 4-Cl | H | 7.91 (s, 1H), 7.76 (s, 1H), 7.68 (d, 2H), 7.49-7.47 (m, 2H), 7.38 (d, 1H), 7.22 (d, 1H), 7.14-7.11 (m, 2H), 6.68-6.62 (m, 2H), 6.49 (d, 1H), 5.09 (q, 1H), 4.85 (d, 1H), 3.72 (d, 1H), 1.38 (d, 3H). |
| 90 | CH$_3$ | H | H | H | H | 8.08 (s, 1H), 7.82 (d, 2H), 7.61 (s, 1H), 7.56-7.36 (m, 5H), 6.83 (t, 2H), 6.46 (s, 1H), 5.07 (q, 1H), 4.75 (d, 1H), 3.73 (d, 1H), 2.47 (s, 3H), 1.32 (d, 3H). |
| 91 | CF$_2$CF$_2$CF$_3$ | H | H | H | H | 8.00 (d, 1H), 7.82 (d, 1H), 7.58-7.39 (m, 6H), 6.82 (m, 1H), 6.73-6.67 (m, 2H), 5.77 (bs, 1H), 5.23 (q, 1H), 4.59 (d, 1H), 3.48 (d, 1H), 1.39 (d, 3H). |
| 92 | NO$_2$ | H | 4-Cl | H | H | 8.34 (s, 1H), 7.98-7.94 (m, 1H), 7.82 (s, 2H), 7.70 (s, 1H), 7.59 (d, 1H), 7.51 (q, 1H), 6.83 (t, 2H), 6.70 (s, 1H), 5.13 (q, 1H), 4.91 (d, 1H), 3.71 (d, 1H), 1.38 (d, 3H). |

EXAMPLES 93 TO 118

Compounds 93 to 118, represented by the following Chemical Formula 7,

[Chemical Formula 7]

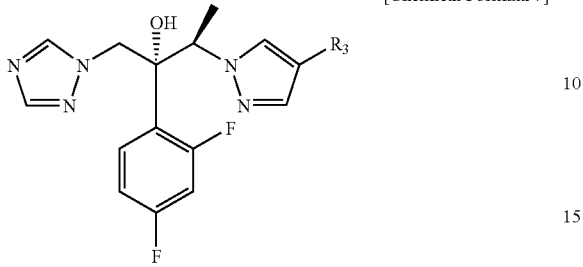

which corresponds to Chemical Formula 1 wherein $R_2$ and $R_4$ are hydrogen and $R_3$ is non-substituted or substituted heteroaryl, were prepared in a manner similar to that of Example 1. Substituents used for the compounds are summarized in Table 4, below.

TABLE 4

| EXAMPLES | $R_3$ | $^1$H-NMR (300 MHz, CDCl$_3$) δ |
|---|---|---|
| 93 | 2-pyridyl | 8.60-8.58 (m, 1 H), 8.30 (s, 1 H), 8.07 (s, 1 H), 7.83 (s, 1 H), 7.71-7.66 (m, 2 H), 7.54-7.49 (m, 2 H), 7.16-7.13 (m, 1 H), 6.82-6.77 (m, 2 H), 5.74 (bs, 1 H), 5.10 (q, 1 H), 4.91 (d, 1 H), 3.70 (d, 1 H), 1.38 (d, 3 H). |
| 94 | 3-pyridyl | 8.45 (s, 1 H), 8.52 (d, 1 H), 8.07 (s, 1 H), 7.90-7.84 (m, 2 H), 7.70 (s, 1 H), 7.52 (q, 1 H), 7.41-7.37 (m, 1 H), 7.32-7.29 (m, 1 H), 6.86-6.78 (m, 2 H), 5.71 (bs, 1 H), 5.13 (q, 1 H), 4.91 (d, 1 H), 3.71 (d, 1 H), 1.39 (3 H). |
| 95 | 4-pyridyl | 8.58 (d, 2 H), 8.12 (s, 1 H), 7.94 (s, 1 H), 7.80 (s, 1 H), 7.68 (s, 1 H), 7.54-7.46 (m, 1 H), 7.42-7.40 (dd, 2 H), 6.83-6.77 (m, 2 H), 5.68 (bs, 1 H), 5.12 (q, 1 H), 4.91 (d, 1 H), 3.69 (d, 1 H), 1.38 (d, 3 H). |
| 96 | 5-F-2-pyridyl | 8.96 (s, 1 H), 8.35 (s, 1 H), 8.11 (s, 1 H), 7.58-7.50 (m, 3 H), 7.40 (s, 1 H), 7.15 (d, 1 H), 6.77-6.71 (m, 2 H), 5.72 (bs, 1 H), 5.11 (q, 1 H), 4.89 (d, 1 H), 3.72 (d, 1 H), 1.38 (d, 3 H). |
| 97 | 5-Cl-2-pyridyl | 9.05 (s, 1 H), 8.41 (s, 1 H), 8.13 (s, 1 H), 7.58-7.50 (m, 3 H), 7.40 (s, 1 H), 7.15 (d, 1 H), 6.77-6.71 (m, 2 H), 5.72 (bs, 1 H), 5.12 (q, 1 H), 4.89 (d, 1 H), 3.71 (d, 1 H), 1.39 (d, 3 H). |
| 98 | 5-CN-2-pyridyl | 9.07 (s, 1 H), 8.35 (s, 1 H), 8.11 (s, 1 H), 7.58-7.50 (m, 3 H), 7.40 (s, 1 H), 7.15 (d, 1 H), 6.77-6.71 (m, 2 H), 5.72 (bs, 1 H), 5.11 (q, 1 H), 4.89 (d, 1 H), 3.72 (d, 1 H), 1.38 (d, 3 H). |
| 99 | 5-NO$_2$-2-pyridyl | 9.15 (s, 1 H), 8.51 (s, 1 H), 8.13 (s, 1 H), 7.55-7.50 (m, 3 H), 7.41 (s, 1 H), 7.17 (d, 1 H), 6.79-6.71 (m, 2 H), 5.70 (bs, 1 H), 5.12 (q, 1 H), 4.87 (d, 1 H), 3.70 (d, 1 H), 1.38 (d, 3 H). |
| 100 | 3-Cl-5-CF$_3$-2-pyridyl | 8.74 (s, 1 H), 8.58 (s, 1 H), 8.41 (s, 1 H), 7.96 (s, 1 H), 7.83 (s, 1 H), 7.65 (s, 1 H), 7.54-7.46 (m, 1 H), 6.84-6.77 (m, 2 H), 5.70 (s, 1 H), 5.14 (q, 1 H), 4.92 (d, 1 H), 3.72 (d, 1 H), 1.39 (s, 3 H). |
| 101 | 3-Me-5-CN-2-pyridyl | 8.54 (s, 1 H), 8.32 (s, 1 H), 8.25 (s, 1 H), 7.86 (s, 1 H), 7.73 (s, 1 H), 7.61 (s, 1 H), 7.51-7.46 (m, 1 H), 6.84-6.77 (m, 2 H), 5.68 (s, 1 H), 5.13 (q, 1 H), 4.91 (d, 1 H), 3.72 (d, 1 H), 1.38 (s, 3 H). |

TABLE 4-continued

| EXAMPLES | R₃ | ¹H-NMR (300 MHz, CDCl₃) δ |
|---|---|---|
| 102 | 2,3-dimethyl-5-chloropyridin-yl | 8.44 (s, 1 H), 8.27 (s, 1 H), 8.21 (s, 1 H), 7.86 (s, 1 H), 7.70 (s, 1 H), 7.59 (s, 1 H), 7.49-7.46 (m, 1 H), 6.83-6.77 (m, 2 H), 5.67 (s, 1 H), 5.12 (q, 1 H), 4.90 (d, 1 H), 3.73 (d, 1 H), 1.38 (s, 3 H). |
| 103 | 2-methyl-3-nitro-5-fluoropyridin-yl | 8.94 (s, 1 H), 8.68 (s, 1 H), 8.47 (s, 1 H), 7.96 (s, 1 H), 7.82 (s, 1 H), 7.67 (s, 1 H), 7.53-7.46 (m, 1 H), 6.84-6.77 (m, 2 H), 5.70 (s, 1 H), 5.14 (q, 1 H), 4.92 (d, 1 H), 3.72 (d, 1 H), 1.39 (s, 3 H). |
| 104 | 2,3-dimethyl-5-nitropyridin-yl | 8.54 (s, 1 H), 8.32 (s, 1 H), 8.25 (s, 1 H), 7.86 (s, 1 H), 7.73 (s, 1 H), 7.61 (s, 1 H), 7.51-7.46 (m, 1 H), 6.84-6.77 (m, 2 H), 5.68 (s, 1 H), 5.13 (q, 1 H), 4.91 (d, 1 H), 3.72 (d, 1 H), 1.37 (s, 3 H). |
| 105 | 3-methyl-5-fluoropyridin-yl | 8.72 (s, 1 H), 8.52 (d, 1 H), 8.07 (s, 1 H), 7.90-7.84 (m, 2 H), 7.70 (s, 1 H), 7.52 (q, 1 H), 7.41-7.37 (m, 1 H), 7.32-7.29 (m, 1 H), 6.85-6.78 (m, 2 H), 5.71 (bs, 1 H), 5.13 (q, 1 H), 4.91 (d, 1 H), 3.81 (d, 1 H), 1.39 (d, 3 H). |
| 106 | 3-methyl-5-chloropyridin-yl | 8.75 (s, 1 H), 8.51 (d, 1 H), 8.17 (s, 1 H), 7.95-7.87 (m, 2 H), 7.71 (s, 1 H), 7.50 (q, 1 H), 7.41-7.37 (m, 1 H), 7.30-7.29 (m, 1 H), 6.87-6.78 (m, 2 H), 5.72 (bs, 1 H), 5.11 (q, 1 H), 4.90 (d, 1 H), 3.71 (d, 1 H), 1.38 (d, 3 H). |
| 107 | 3-methyl-5-cyanopyridin-yl | 8.78 (s, 1 H), 8.53 (d, 1 H), 8.17 (s, 1 H), 7.96-7.87 (m, 2 H), 7.72 (s, 1 H), 7.49 (q, 1 H), 7.40-7.37 (m, 1 H), 7.30-7.29 (m, 1 H), 6.88-6.78 (m, 2 H), 5.72 (bs, 1 H), 5.12 (q, 1 H), 4.91 (d, 1 H), 3.70 (d, 1 H), 1.38 (d, 3 H). |
| 108 | 3-methyl-4-fluoropyridin-yl | 8.69 (s, 1 H), 8.51 (d, 1 H), 8.08 (s, 1 H), 7.91-7.84 (m, 2 H), 7.75 (s, 1 H), 7.51 (q, 1 H), 7.40-7.37 (m, 1 H), 7.32-7.29 (m, 1 H), 6.85-6.75 (m, 2 H), 5.72 (bs, 1 H), 5.13 (q, 1 H), 4.93 (d, 1 H), 3.72 (d, 1 H), 1.38 (d, 3 H). |
| 109 | 2-methyl-4-chloropyridin-yl | 8.79 (s, 1 H), 8.55 (d, 1 H), 8.12 (s, 1 H), 7.91-7.87 (m, 2 H), 7.70 (s, 1 H), 7.50 (q, 1 H), 7.40-7.37 (m, 1 H), 7.29-7.29 (m, 1 H), 6.85-6.78 (m, 2 H), 5.72 (bs, 1 H), 5.13 (q, 1 H), 4.91 (d, 1 H), 3.70 (d, 1 H), 1.37 (d, 3 H). |
| 110 | 2-methyl-4-cyanopyridin-yl | 8.82 (s, 1 H), 8.49 (d, 1 H), 8.19 (s, 1 H), 7.95-7.87 (m, 2 H), 7.71 (s, 1 H), 7.51 (q, 1 H), 7.38-7.37 (m, 1 H), 7.30-7.29 (m, 1 H), 6.86-6.78 (m, 2 H), 5.71 (bs, 1 H), 5.11 (q, 1 H), 4.90 (d, 1 H), 3.73 (d, 1 H), 1.38 (d, 3 H). |
| 111 | 2-methyl-5-fluoropyridin-yl | 8.94 (s, 1 H), 8.32 (s, 1 H), 8.15 (s, 1 H), 7.57-7.50 (m, 3 H), 7.43 (s, 1 H), 7.12 (d, 1 H), 6.76-6.71 (m, 2 H), 5.71 (bs, 1 H), 5.12 (q, 1 H), 4.89 (d, 1 H), 3.71 (d, 1 H), 1.39 (d, 3 H). |

TABLE 4-continued

| EXAMPLES | R₃ | ¹H-NMR (300 MHz, CDCl₃) δ |
|---|---|---|
| 112 | 4-methyl-3-chloropyridinyl | 9.02 (s, 1 H), 8.43 (s, 1 H), 8.11 (s, 1 H), 7.56-7.50 (m, 3 H), 7.41 (s, 1 H), 7.15 (d, 1 H), 6.77-6.70 (m, 2 H), 5.71 (bs, 1 H), 5.12 (q, 1 H), 4.85 (d, 1 H), 3.71 (d, 1 H), 1.38 (d, 3 H). |
| 113 | 4-methyl-3-cyanopyridinyl | 9.05 (s, 1 H), 8.32 (s, 1 H), 8.10 (s, 1 H), 7.57-7.50 (m, 3 H), 7.41 (s, 1 H), 7.14 (d, 1 H), 6.77-6.70 (m, 2 H), 5.72 (bs, 1 H), 5.12 (q, 1 H), 4.87 (d, 1 H), 3.73 (d, 1 H), 1.38 (d, 3 H). |
| 114 | 4-methyl-3,5-difluoropyridinyl | 8.99 (s, 1 H), 8.36 (s, 1 H), 8.18 (s, 1 H), 7.52-7.48 (m, 3 H), 7.45 (s, 1 H), 7.11 (d, 1 H), 6.76-6.68 (m, 2 H), 5.70 (bs, 1 H), 5.12 (q, 1 H), 4.88 (d, 1 H), 3.72 (d, 1 H), 1.40 (d, 3 H). |
| 115 | pyrimidinyl | 9.32 (s, 1 H), 8.84 (d, 1 H), 8.15 (s, 1 H), 8.11 (s, 1 H), 7.58 (d, 1 H), 7.50 (s, 1 H), 7.40 (s, 1 H), 7.15 (s, 1 H), 6.67-6.61 (m, 2 H), 5.71 (bs, 1 H), 5.12 (q, 1 H), 4.89 (d, 1 H), 3.82 (d, 1 H), 1.41 (s, 3 H). |
| 116 | isoquinolinyl | 8.91 (d, 1 H), 8.21-8.16 (m, 2 H), 8.10 (s, 1 H), 7.93 (s, 1 H), 7.87 (s, 1 H), 7.76 (t, 1 H), 7.71 (s, 1 H), 7.61-7.58 (m, 2 H), 7.40 (d, 1 H), 6.85-6.79 (m, 2 H), 5.79 (s, 1 H), 5.19 (q, 1 H), 4.96 (d, 1 H), 3.82 (d, 1 H), 1.45 (s, 3 H). |
| 117 | quinoxalinyl | 9.11 (s, 1 H), 8.52 (s, 1 H), 8.30 (s, 1 H), 8.10-8.01 (m, 2 H), 7.83-7.68 (m, 3 H), 7.53 (t, 1 H), 7.71 (s, 1 H), 6.82-6.78 (m, 2 H), 5.69 (s, 1 H), 5.18 (q, 1 H), 4.97 (d, 1 H), 3.75 (d, 1 H), 1.43 (s, 3 H). |
| 118 | benzofuranyl | 8.14 (s, 1 H), 7.96 (s, 1 H), 7.83 (s, 1 H), 7.69 (s, 1 H), 7.56-7.48 (m, 3 H), 7.27-7.23 (m, 2 H), 6.81-6.78 (m, 2 H), 5.68 (s, 1 H), 5.11 (q, 1 H), 4.93 (d, 1 H), 3.70 (d, 1 H), 1.39 (s, 3 H). |

FORMULATION EXAMPLE 1

Tablet (2R,3R)-2-(2,4-difluorophenyl)-3-(4-(4-nitrophenyl)-1H-pyrazole-1-yl)-1-(1H-1,2,4-triazole-1-yl)butane-2-ol (50 mg), prepared in Example 1, and magnesium stearate (20 mg) were granulated with soluble starch (35 mg), and the granules were dried and mixed with lactose (65 mg) and corn starch (30 mg) for 30 min using a mechanical shaker and a mixer. The mixture was pressed into tablets.

TEST EXAMPLE 1

In Vitro Assay for Antifungal Activity

Fungal strains to be tested were inoculated onto Sabouraud dextrose agar, YM agar, and Potato dextrose agar and sufficiently cultured at 35° C. for two to three days. Individual single colonies of the yeast fungi selected out of the cultured strains were sufficiently suspended in 5 ml of 0.85% sterile physiological saline, followed by correction to adjust the absorbance thereof at 530 nm to 0.108. The suspensions were diluted serially by 1:50 and then 1:20 in RPMI 1640 media to prepare liquid inocula ranging in cell count from $1.0 \times 10^3$ to $5.0 \times 10^3$ CFU/ml.

Antifungal samples were prepared by diluting the compounds of the present inventions in RPMI 1640 media to serial concentrations ranging from 0.0625 to 32 μg/ml. As a vehicle, DMSO was contained in a final concentration of 1% (V/V) in the antifungal samples. 0.1 ml of each of the dilutions in series was added to equal volume of each of the fungal inocula.

At the concentrations provided, the fungi were observed with the naked eye for the growth of all yeasts except for *Cryptococcus neoformans* after 24 hours. Concentrations of the compounds at which 50% of the fungi were inhibited compared to the negative control were determined using the growth indicator alamarblue. All tests were conducted in duplicate for each test group, and the results are given in Table 5, below.

TABLE 5

| | Results of Assay for Antifungal Activity (MIC µg/ml) | | | | | | | |
| | Examples | | | | | | | |
| | 2 | 3 | 8 | 9 | 14 | 15 | 17 | Fluconazole |
|---|---|---|---|---|---|---|---|---|
| Candida albicans | ≦0.015 | ≦0.015 | ≦0.015 | ≦0.015 | ≦0.015 | ≦0.015 | ≦0.015 | 4 |
| Candida glabrata | 2 | 2 | 2 | 1 | 2 | 2 | 4 | >32 |
| Candida krusei | 0.5 | 1 | 0.5 | 0.25 | 0.25 | 0.5 | 0.25 | >32 |
| Candida tropicalis | 0.25 | 1 | 0.25 | 0.063 | 0.031 | 0.125 | 0.125 | >8 |
| Candida parapsilosis | ≦0.015 | 0.031 | ≦0.015 | ≦0.015 | ≦0.015 | ≦0.015 | ≦0.015 | >8 |
| Cryptococcus neoformans | 0.25 | 0.125 | 0.031 | 0.25 | 0.25 | 0.125 | 0.031 | 8 |
| Aspergillus fumigatus | 1 | 0.5 | 1 | 2 | 1 | 1 | 2 | >128 |
| Aspergillus flavus | 4 | 4 | 8 | 8 | 4 | 4 | 8 | >128 |
| Aspergillus terreus | 4 | 2 | 2 | 4 | 2 | 1 | 2 | >128 |

TEST EXAMPLES 2

In Vivo Assay for Antifungal Activity (Systemic Candidiasis)

Azole compounds synthesized in Examples were assayed for antifungal activity in vivo.

A suspension containing *Candida albicans* in a concentration ranging from $7 \times 10^7$ to $8 \times 10^7$ cfu/ml was intravenously injected at a dose of 0.1 ml/head into 10 male mice. 2 hrs after the injection, the compounds of the present inventions were orally administered at a dose of 20 mg/kg to respective mice in groups of 10. The compounds were administered once a day for seven days. The periods of time for which the infected mice lived were counted. The number of mice that survived the fungal infection was represented as % survival for each test group.

All of the animals in control group were observed to die between 4 to 9 days after the infection. Animals treated with compounds of Example 14, 15 or 17 showed 40 to 60% survival at 28 days after the infection, whereas fluconazole protected only 10% on day 28.

TEST EXAMPLE 3

Assay for Acute Toxicity in Mice

From acute toxicity tests using the suspensions of compounds of Examples 14 and 17 in an aqueous 0.5% methylcellulose base, mice were observed not to suffer from any toxic syndromes, including severe changes to living states and organs, up to a dose of 2000 mg/kg for two weeks upon oral administration.

INDUSTRIAL APPLICABILITY

As described hitherto, the present invention provides the triazole derivatives of Chemical Formula or pharmaceutically acceptable salts thereof which are very useful as active ingredients for antifungal agents because they have excellent inhibitory activity against a broad spectrum of fungi and show far higher therapeutic effects on fungal infection than do conventional drugs, in addition to being safe to the body, high doses being allowable for oral administration.

The invention claimed is:
1. A triazole compound represented by the following chemical formula 1, or a pharmaceutically acceptable salt thereof:

Chemical Formula 1:

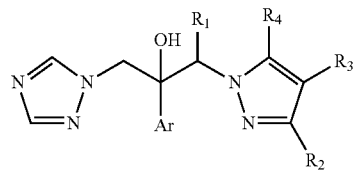

wherein,
Ar is phenyl substituted with at least one halogen or trifluoromethyl group;
$R_1$ is fluorine, or a $C_1$-$C_4$ lower alkyl;
$R_2$ is a halogen; a $C_1$-$C_4$ lower alkyl; a $C_1$-$C_4$ alkoxy; $C_1$-$C_4$ a haloalkyl; a $C_3$-$C_6$ cycloalkyl; a nitro; a cyano; an amino; a hydroxy; a $C_6$-$C_{20}$ aryl, non-substituted or substituted with at least one radical selected from the group consisting of a $C_1$-$C_4$ lower alkyl, a $C_1$-$C_4$ alkoxy, a halogen, a cyano, a nitro, a $C_1$-$C_4$ haloalkyl, a $C_1$-$C_4$ haloalkoxy, morpholine, pyrrolidine, piperidine,

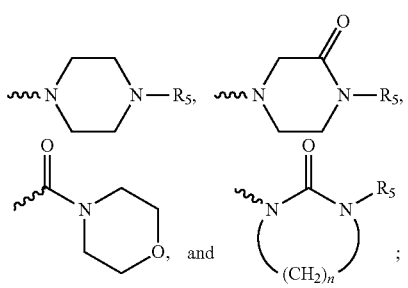

or $C_6$-$C_{20}$ heteroaryl, non-substituted or substituted with at least one substituent selected from the group consisting of a $C_1$-$C_4$ lower alkyl, a $C_1$-$C_4$ alkoxy, a halogen, a cyano, a nitro, a $C_1$-$C_4$ haloalkyl, and a $C_1$-$C_4$ haloalkoxy, $R_3$ and $R_4$ may be different or the same and are hydrogen; a halogen; a $C_1$-$C_4$ lower alkyl; a $C_1$-$C_4$ alkoxy; a $C_1$-$C_4$ haloalkyl; a $C_3$-$C_6$ cycloalkyl; a nitro; a cyano; an amino; a hydroxy; a $C_6$-$C_{20}$ aryl, a non-substituted or substituted with at least one radical selected from the group consisting of a $C_1$-$C_4$ lower alkyl, a $C_1$-$C_4$ alkoxy, a halogen, a cyano, a nitro, a $C_1$-$C_4$ haloalkyl, a $C_1$-$C_4$ haloalkoxy, morpholine, pyrrolidine, piperidine,

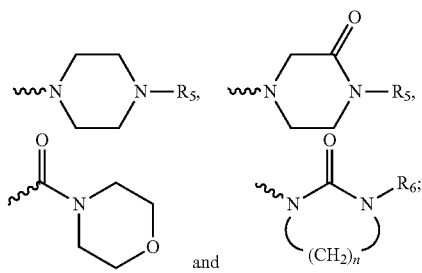

or a $C_6$-$C_{20}$ heteroaryl, non-substituted or substituted with at least one substituent selected from the group consisting of a $C_1$-$C_4$ lower alkyl, a $C_1$-$C_4$ alkoxy, a halogen, a cyano, a nitro, a $C_1$-$C_4$ haloalkyl, and a $C_1$-$C_4$ haloalkoxy, $R_5$ is a hydrogen, a $C_1$-$C_4$ alkyl, a $C_1$-$C_4$ alkoxy or a $C_1$-$C_5$ hydroxy alkyl, and n is an integer from 1 to 3.

2. The triazole compound or pharmaceutically acceptable salt thereof according to claim 1, wherein Ar is phenyl substituted with at least one halogen, $R_1$ is a $C_1$-$C_4$ lower alkyl, $R_2$ is a $C_1$-$C_4$ lower alkyl; a $C_1$-$C_4$ haloalkyl; a nitro; a cyano; an amino; a hydroxy; phenyl, non-substituted or substituted with at least one radical selected from the group consisting of a $C_1$-$C_4$ lower alkyl, a $C_1$-$C_4$ alkoxy, a halogen, a cyano, a nitro, trifluoromethyl, trifluoromethoxy, morpholine, pyrrolidine,

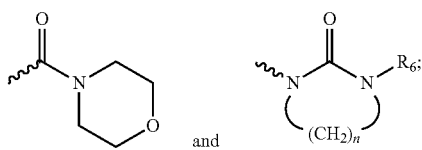

or a heteroaryl selected from the group consisting of pyridine, pyrimidine, quinoline, quinoxaline and benzofuran, said heteroaryl being non-substituted or substituted with at least one radical selected from the group consisting of a $C_1$-$C_4$ lower alkyl, a $C_1$-$C_4$ alkoxy, a halogen, a cyano, a nitro, trifluoromethyl and trifluoromethoxy, $R_3$ and $R_4$ may be different or the same and are each hydrogen; a $C_1$-$C_4$ lower alkyl; a $C_1$-$C_4$ haloalkyl; a nitro; a cyano; an amino; a hydroxy; phenyl, non-substituted or substituted with at least one radical selected from the group consisting of a $C_1$-$C_4$ lower alkyl, a $C_1$-$C_4$ alkoxy, a halogen, a cyano, a nitro, trifluoromethyl, trifluoromethoxy, morpholine, pyrrolidine,

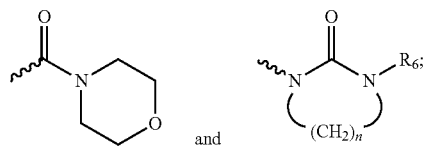

or a heteroaryl selected from the group consisting of pyridine, pyrimidine, quinoline, quinoxaline and benzofuran, said heteroaryl being non-substituted or substituted with at least one radical selected from the group consisting of a $C_1$-$C_4$ lower alkyl, a $C_1$-$C_4$ alkoxy, a halogen, a cyano, a nitro, trifluoromethyl and trifluoromethoxy, $R_5$ is hydrogen, a $C_1$-$C_4$ alkyl, or a $C_1$-$C_5$ hydroxy alkyl, and n is an integer of 2 or 3.

3. A triazole compound or a pharmaceutically acceptable salt thereof, said triazole compound being selected from the group consisting of:

1) (2R,3R)-3-(4-(4-fluorophenyl)-1H-pyrazole-1-yl)-2-(2,4-difluorophenyl)-1-(1H-1,2,4-triazole-1-yl)butane-2-ol,
2) (2R,3R)-3-(4-phenyl-1H-pyrazole-1-yl)-2-(2,4-difluorophenyl)-1-(1H-1,2,4-triazole-1-yl)butane-2-ol,
3) (2R,3R)-3-(4-(2-fluorophenyl)-1H-pyrazole-1-yl)-2-(2,4-difluorophenyl)-1-(1H-1,2,4-triazole-1-yl)butane-2-ol,
4) (2R,3R)-3-(4-(2-chlorophenyl)-1H-pyrazole-1-yl)-2-(2,4-difluorophenyl)-1-(1H-1,2,4-triazole-1-yl)butane-2-ol,
5) (2R,3R)-3-(4-(2-bromophenyl)-1H-pyrazole-1-yl)-2-(2,4-difluorophenyl)-1-(1H-1,2,4-triazole-1-yl)butane-2-ol,
6) (2R,3R)-3-(4-(2-cyanophenyl)-1H-pyrazole-1-yl)-2-(2,4-difluorophenyl)-1-(1H-1,2,4-triazole-1-yl)butane-2-ol,
7) (2R,3R)-3-(4-(2-nitrophenyl)-1H-pyrazole-1-yl)-2-(2,4-difluorophenyl)-1-(1H-1,2,4-triazole-1-yl)butane-2-ol,
8) (2R,3R)-3-(4-(3-fluorophenyl)-1H-pyrazole-1-yl)-2-(2,4-difluorophenyl)-1-(1H-1,2,4-triazole-1-yl)butane-2-ol,
9) (2R,3R)-3-(4-(3-chlorophenyl)-1H-pyrazole-1-yl)-2-(2,4-difluorophenyl)-1-(1H-1,2,4-triazole-1-yl)butane-2-ol,
10) (2R,3R)-3-(4-(3-bromophenyl)-1H-pyrazole-1-yl)-2-(2,4-difluorophenyl)-1-(1H-1,2,4-triazole-1-yl)butane-2-ol,
11) (2R,3R)-3-(4-(3-trifluoromethylphenyl)-1H-pyrazole-1-yl)-2-(2,4-difluorophenyl)-1-(1H-1,2,4-triazole-1-yl)butane-2-ol,
12) (2R,3R)-3-(4-(3-cyanophenyl)-1H-pyrazole-1-yl)-2-(2,4-difluorophenyl)-1-(1H-1,2,4-triazole-1-yl)butane-2-ol,
13) (2R,3R)-3-(4-(3-nitrophenyl)-1H-pyrazole-1-yl)-2-(2,4-difluorophenyl)-1-(1H-1,2,4-triazole-1-yl)butane-2-ol,
14) (2R,3R)-3-(4-(4-chlorophenyl)-1H-pyrazole-1-yl)-2-(2,4-difluorophenyl)-1-(1H-1,2,4-triazole-1-yl)butane-2-ol,
15) (2R,3R)-3-(4-(4-bromophenyl)-1H-pyrazole-1-yl)-2-(2,4-difluorophenyl)-1-(1H-1,2,4-triazole-1-yl)butane-2-ol,
16) (2R,3R)-3-(4-(4-methoxyphenyl)-1H-pyrazole-1-yl)-2-(2,4-difluorophenyl)-1-(1H-1,2,4-triazole-1-yl)butane-2-ol, 17) (2R,3R)-3-(4-(4-nitrophenyl)-1H-pyrazole-1-yl)-2-(2,4-difluorophenyl)-1-(1H-1,2,4-triazole-1-yl)butane-2-ol,
18) (2R,3R)-3-(4-(4-trifluoromethylphenyl)-1H-pyrazole-1-yl)-2-(2,4-difluorophenyl)-1-(1H-1,2,4-triazole-1-yl)butane-2-ol,
19) (2R,3R)-3-(4-(4-cyanophenyl)-1H-pyrazole-1-yl)-2-(2,4-difluorophenyl)-1-(1H-1,2,4-triazole-1-yl)butane-2-ol,
20) (2R,3R)-3-(4-(4-trifluoromethoxyphenyl)-1H-pyrazole-1-yl)-2-(2,4-difluorophenyl)-1-(1H-1,2,4-triazole-1-yl)butane-2-ol,
21) (2R,3R)-3-(4-(4-morpholinocarbonylphenyl)-1H-pyrazole-1-yl)-2-(2,4-difluorophenyl)-1-(1H-1,2,4-triazole-1-yl)butane-2-ol,
22) (2R,3R)-3-(4-(4-imidazolidin-2-on-l-ylphenyl)-1H-pyrazole-1-yl)-2-(2,4-difluorophenyl)-1-(1H-1,2,4-triazole-1-yl)butane-2-ol,
23) (2R,3R)-3-(4-(4-3-methyl-imidazolidin-2-on-l-ylphenyl)-1H-pyrazole-1-yl)-2-(2,4-difluorophenyl)-1-(1H-1,2,4-triazole-1-yl)butane-2-ol,
24) (2R,3R)-3-(4-(4-3-isopropyl-imidazolidin-2-on-l-ylphenyl)-1H-pyrazole-1-yl)-2-(2,4-difluorophenyl)-1-(1H-1,2,4-triazole-1-yl)butane-2-ol,
25) (2R,3R)-3-(4-(4-3-hydro-tetrahydropyrimidin-2(1H)-on-1-ylphenyl)-1H-pyrazole-1-yl)-2-(2,4-difluorophenyl)-1-(1H-1,2,4-triazole-1-yl)butane-2-ol,
26) (2R,3R)-3-(4-(4-3-methyl-tetrahydropyrimidin-2(1H)-on-1-ylphenyl)-1H-pyrazole-1-yl)-2-(2,4-difluorophenyl)-1-(1H-1,2,4-triazole-1-yl)butane-2-ol,
27) (2R,3R)-3-(4-(3,5-difluorophenyl)-1H-pyrazole-1-yl)-2-(2,4-difluorophenyl)-1-(1H-1,2,4-triazole-1-yl)butane-2-ol,
28) (2R,3R)-3-(4-(3-chloro-5-fluorophenyl)-1H-pyrazole-1-yl)-2-(2,4-difluorophenyl)-1-(1H-1,2,4-triazole-1-yl)butane-2-ol,
29) (2R,3R)-3-(4-(3-chloro-4-methyl-5-fluorophenyl)-1H-pyrazole-1-yl)-2-(2,4-difluorophenyl)-1-(1H-1,2,4-triazole-1-yl)butane-2-ol,
30) (2R,3R)-3-(4-(2,4-difluorophenyl)-1H-pyrazole-1-yl)-2-(2,4-difluorophenyl)-1-(1H-1,2,4-triazole-1-yl)butane-2-ol,
31) (2R,3R)-3-(4-(4-fluoro-3-methylphenyl)-1H-pyrazole-1-yl)-2-(2,4-difluorophenyl)-1-(1H-1,2,4-triazole-1-yl)butane-2-ol,
32) (2R,3R)-3-(4-(4-fluoro-2-methylphenyl)-1H-pyrazole-1-yl)-2-(2,4-difluorophenyl)-1-(1H-1,2,4-triazole-1-yl)butane-2-ol,
33) (2R,3R)-3-(4-(4-fluoro-2-methoxyphenyl)-1H-pyrazole-1-yl)-2-(2,4-difluorophenyl)-1-(1H-1,2,4-triazole-1-yl)butane-2-ol,
34) (2R,3R)-3-(4-(4-fluoro-3-methoxyphenyl)-1H-pyrazole-1-yl)-2-(2,4-difluorophenyl)-1-(1H-1,2,4-triazole-1-yl)butane-2-ol,
35) (2R,3R)-3-(4-(3-chloro-4-fluorophenyl)-1H-pyrazole-1-yl)-2-(2,4-difluorophenyl)-1-(1H-1,2,4-triazole-1-yl)butane-2-ol,
36) (2R,3R)-3-(4-(4-chloro-2-fluorophenyl)-1H-pyrazole-1-yl)-2-(2,4-difluorophenyl)-1-(1H-1,2,4-triazole-1-yl)butane-2-ol,
37) (2R,3R)-3-(4-(3,4-dichlorophenyl)-1H-pyrazole-1-yl)-2-(2,4-difluorophenyl)-1-(1H-1,2,4-triazole-1-yl)butane-2-ol,
38) (2R,3R)-3-(4-(4-chloro-2-methylphenyl)-1H-pyrazole-1-yl)-2-(2,4-difluorophenyl)-1-(1H-1,2,4-triazole-1-yl)butane-2-ol,
39) (2R,3R)-3-(4-(4-chloro-3-methylphenyl)-1H-pyrazole-1-yl)-2-(2,4-difluorophenyl)-1-(1H-1,2,4-triazole-1-yl)butane-2-ol,
40) (2R,3R)-3-(4-(4-chloro-3-methoxyphenyl)-1H-pyrazole-1-yl)-2-(2,4-difluorophenyl)-1-(1H-1,2,4-triazole-1-yl)butane-2-ol,
41) (2R,3R)-3-(4-(4-chloro-3-cyanophenyl)-1H-pyrazole-1-yl)-2-(2,4-difluorophenyl)-1-(1H-1,2,4-triazole-1-yl)butane-2-ol,
42) (2R,3R)-3-(4-(4-chloro-3-nitrophenyl)-1H-pyrazole-1-yl)-2-(2,4-difluorophenyl)-1-(1H-1,2,4-triazole-1-yl)butane-2-ol,
43) (2R,3R)-3-(4-(3,5-dichlorophenyl)-1H-pyrazole-1-yl)-2-(2,4-difluorophenyl)-1-(1H-1,2,4-triazole-1-yl)butane-2-ol,
44) (2R,3R)-3-(4-(4-cyano-3-fluorophenyl)-1H-pyrazole-1-yl)-2-(2,4-difluorophenyl)-1-(1H-1,2,4-triazole-1-yl)butane-2-ol,
45) (2R,3R)-3-(4-(4-morpholinophenyl)-1H-pyrazole-1-yl)-2-(2,4-difluorophenyl)-1-(1H-1,2,4-triazole-1-yl)butane-2-ol,
46) (2R,3R)-3-(4-(3-morpholinophenyl)-1H-pyrazole-1-yl)-2-(2,4-difluorophenyl)-1-(1H-1,2,4-triazole-1-yl)butane-2-ol,
47) (2R,3R)-3-(4-(2-morpholinophenyl)-1H-pyrazole-1-yl)-2-(2,4-difluorophenyl)-1-(1H-1,2,4-triazole-1-yl)butane-2-ol,
48) (2R,3R)-2-(2,4-difluorophenyl)-3-(4-(3-(pyrrolidin-1-yl)phenyl)-1H-pyrazol-1-yl)-1-(1H-1,2,4-triazol-1-yl)butan-2-ol,
49) (2R,3R)-3-(3-methyl-4-(2-chlorophenyl)-1H-pyrazole-1-yl)-2-(2,4-difluorophenyl)-1-(1H-1,2,4-triazole-1-yl)butane-2-ol,
50) (2R,3R)-3-(3-methyl-4-(2-bromophenyl)-1H-pyrazole-1-yl)-2-(2,4-difluorophenyl)-1-(1H-1,2,4-triazole-1-yl)butane-2-ol,
51) (2R,3R)-3-(3-methyl-4-(3-fluorophenyl)-1H-pyrazole-1-yl)-2-(2,4-difluorophenyl)-1-(1H-1,2,4-triazole-1-yl)butane-2-ol,
52) (2R,3R)-3-(3-methyl-4-(3-chlorophenyl)-1H-pyrazole-1-yl)-2-(2,4-difluorophenyl)-1-(1H-1,2,4-triazole-1-yl)butane-2-ol,
53) (2R,3R)-3-(3-methyl-4-(3-trifluoromethylphenyl)-1H-pyrazole-1-yl)-2-(2,4-difluorophenyl)-1-(1H-1,2,4-triazole-1-yl)butane-2-ol,
54) (2R,3R)-3-(4-(3-fluorophenyl)-5-methyl-1H-pyrazole-1-yl)-2-(2,4-difluorophenyl)-1-(1H-1,2,4-triazole-1-yl)butane-2-ol,
55) (2R,3R)-3-(4-(3-chlorophenyl)-5-methyl-1H-pyrazole-1-yl)-2-(2,4-difluorophenyl)-1-(1H-1,2,4-triazole-1-yl)butane-2-ol,
56) (2R,3R)-3-(3-(4-pyridinyl)-4-(4-trifluoromethylphenyl)-1H-pyrazole-1-yl)-2-(2,4-difluorophenyl)-1-(1H-1,2,4-triazole-1-yl)butane-2-ol,
57) (2R,3R)-3-(3-phenyl-1H-pyrazole-1-yl)-2-(2,4-difluorophenyl)-1-(1H-1,2,4-triazole-1-yl)butane-2-ol,
58) (2R,3R)-3-(3-(2-fluorophenyl)-1H-pyrazole-1-yl)-2-(2,4-difluorophenyl)-1-(1H-1,2,4-triazole-1-yl)butane-2-ol,
59) (2R,3R)-3-(3-(2-chlorophenyl)-1H-pyrazole-1-yl)-2-(2,4-difluorophenyl)-1-(1H-1,2,4-triazole-1-yl)butane-2-ol,
60) (2R,3R)-3-(3-(2-bromophenyl)-1H-pyrazole-1-yl)-2-(2,4-difluorophenyl)-1-(1H-1,2,4-triazole-1-yl)butane-2-ol, 61) (2R,3R)-3-(3-(2-nitrophenyl)-1H-pyrazole-1-yl)-2-(2,4-difluorophenyl)-1-(1H-1,2,4-triazole-1-yl)butane-2-ol, 62) (2R,3R)-3-(3-(2-trifluoromethylphenyl)-1H-pyrazole-1-yl)-2-(2,4-difluorophenyl)-1-(1H-1,2,4-triazole-1-yl)butane-2-ol, 63) (2R,3R)-3-(3-(3-fluorophenyl)-1H-pyrazole-1-yl)-2-(2,4-difluorophenyl)-1-(1H-1,2,4-triazole-1-yl)butane-2-ol, 64) (2R,3R)-3-(3-(3-chlorophenyl)-1H-pyrazole-1-yl)-2-(2,4-difluorophenyl)-1-(1H-1,2,4-triazole-1-yl)butane-2-ol, 65) (2R,3R)-3-(3-(3-bromophenyl)-1H-pyrazole-1-yl)-2-(2,4-difluorophenyl)-1-(1H-1,2,4-triazole-1-yl)butane-2-ol, 66) (2R,3R)-3-(3-(3-nitrophenyl)-1H-pyrazole-1-yl)-2-(2,4-difluorophenyl)-1-(1H-1,2,4-triazole-1-yl)butane-2-ol, 67) (2R,3R)-3-(3-(3-trifluoromethylphenyl)-1H-pyrazole-1-yl)-2-(2,4-difluorophenyl)-1-(1H-1,2,4-triazole-1-yl)butane-2-ol, 68) (2R,3R)-3-(3-(4-fluorophenyl)-1H-pyrazole-1-yl)-2-(2,4-difluorophenyl)-1-(1H-1,2,4-triazole-1-yl)butane-2-ol, 69) (2R,3R)-3-(3-(4-chlorophenyl)-1H-pyrazole-1-yl)-2-(2,4-difluorophenyl)-1-(1H-1,2,4-triazole-1-yl)butane-2-ol, 70) (2R,3R)-3-(3-(4-bromophenyl)-1H-pyrazole-1-yl)-2-(2,4-difluorophenyl)-1-(1H-1,2,4-triazole-1-yl)butane-2-ol, 71) (2R,3R)-3-(3-(4-nitrophenyl)-1H-pyrazole-1-yl)-2-(2,4-difluorophenyl)-1-(1H-1,2,4-triazole-1-yl)butane-2-ol, 72) (2R,3R)-3-(3-(4-trifluoromethylphenyl)-1H-pyrazole-1-yl)-2-(2,4-difluorophenyl)-1-(1H-1,2,4-triazole-1-yl)butane-2-ol, 73) (2R,3R)-3-(3-(4-trifluoromethoxyphenyl)-1H-pyrazole-1-yl)-2-(2,4-difluorophenyl)-1-(1H-1,2,4-triazole-1-yl)butane-2-ol, 74) (2R,3R)-3-(3-(4-cyanophenyl)-1H-pyrazole-1-yl)-2-(2,4-difluorophenyl)-1-(1H-1,2,4-triazole-1-yl)butane-2-ol, 75) (2R,3R)-3-(3-(2,4-difluorophenyl)-1H-pyrazole-1-yl)-2-(2,4-difluorophenyl)-1-(1H-1,2,4-triazole-1-yl)butane-2-ol, 76) (2R,3R)-3-(3-(2,6-difluorophenyl)-1H-pyrazole-1-yl)-2-(2,4-difluorophenyl)-1-(1H-1,2,4-triazole-1-yl)butane-2-ol, 77) (2R,3R)-3-(3-(2,4-dichlorophenyl)-1H-pyrazole-1-yl)-2-(2,4-difluorophenyl)-1-(1H-1,2,4-triazole-1-yl)butane-2-ol, 78) (2R,3R)-3-(3-(3,4-dichlorophenyl)-1H-pyrazole-1-yl)-2-(2,4-difluorophenyl)-1-(1H-1,2,4-triazole-1-yl)butane-2-ol, 79) (2R,3R)-3-(3-(4-fluorophenyl)-4-methyl-1H-pyrazole-1-yl)-2-(2,4-difluorophenyl)-1-(1H-1,2,4-triazole-1-yl)butane-2-ol, 80) (2R,3R)-3-(3-(4-chlorophenyl)-4-methyl-1H-pyrazole-1-yl)-2-(2,4-difluorophenyl)-1-(1H-1,2,4-triazole-1-yl)butane-2-ol, 81) (2R,3R)-3-(3-phenyl-5-methyl-1H-pyrazole-1-yl)-2-(2,4-difluorophenyl)-1-(1H-1,2,4-triazole-1-yl)butane-2-ol, 82) (2R,3R)-3-(3-(4-bromophenyl)-5-methyl-1H-pyrazole-1-yl)-2-(2,4-difluorophenyl)-1-(1H-1,2,4-triazole-1-yl)butane-2-ol, 83) (2R,3R)-3-(5-phenyl-1H-pyrazole-1-yl)-2-(2,4-difluorophenyl)-1-(1H-1,2,4-triazole-1-yl)butane-2-ol, 84) (2R,3R)-3-(5-(2-bromophenyl)-1H-pyrazole-1-yl)-2-(2,4-difluorophenyl)-1-(1H-1,2,4-triazole-1-yl)butane-2-ol, 85) (2R,3R)-3-(5-(3-bromophenyl)-1H-pyrazole-1-yl)-2-(2,4-difluorophenyl)-1-(1H-1,2,4-triazole-1-yl)butane-2-ol, 86) (2R,3R)-3-(5-(4-bromophenyl)-1H-pyrazole-1-yl)-2-(2,4-difluorophenyl)-1-(1H-1,2,4-triazole-1-yl)butane-2-ol, 87) (2R,3R)-3-(5-(4-fluorophenyl)-1H-pyrazole-1-yl)-2-(2,4-difluorophenyl)-1-(1H-1,2,4-triazole-1-yl)butane-2-ol, 88) (2R,3R)-3-(5-(4-chlorophenyl)-1H-pyrazole-1-yl)-2-(2,4-difluorophenyl)-1-(1H-1,2,4-triazole-1-yl)butane-2-ol, 89) (2R,3R)-3-(5-(2,4-dichlorophenyl)-1H-pyrazole-1-yl)-2-(2,4-difluorophenyl)-1-(1H-1,2,4-triazole-1-yl)butane-2-ol, 90) (2R,3R)-3-(3-methyl-5-phenyl-1H-pyrazole-1-yl)-2-(2,4-difluorophenyl)-1-(1H-1,2,4-triazole-1-yl)butane-2-ol, 91) (2R,3R)-3-(3-perfluoropropyl-5-phenyl-1H-pyrazole-1-yl)-2-(2,4-difluorophenyl)-1-(1H-1,2,4-triazole-1-yl)butane-2-ol, 92) (2R,3R)-3-(3-nitro-5-(4-chlorophenyl)-1H-pyrazole-1-yl)-2-(2,4-difluorophenyl)-1-(1H-1,2,4-triazole-1-yl)butane-2-ol, 93) (2R,3R)-3-(4-(pyridine-2-yl)-1H-pyrazole-1-yl)-2-(2,4-difluorophenyl)-1-(1H-1,2,4-triazole-1-yl)butane-2-ol, 94) (2R,3R)-3-(4-(pyridine-3-yl)-1H-pyrazole-1-yl)-2-(2,4-difluorophenyl)-1-(1H-1,2,4-triazole-1-yl)butane-2-ol, 95) (2R,3R)-3-(4-(pyridine-4-yl)-1H-pyrazole-1-yl)-2-(2,4-difluorophenyl)-1-(1H-1,2,4-triazole-1-yl)butane-2-ol, 96) (2R,3R)-3-(4-(5-fluoropyridine-2-yl)-1H-pyrazole-1-yl)-2-(2,4-difluorophenyl)-1-(1H-1,2,4-triazole-1-yl)butane-2-ol, 97) (2R,3R)-3-(4-(5-chloropyridine-2-yl)-1H-pyrazole-1-yl)-2-(2,4-difluorophenyl)-1-(1H-1,2,4-triazole-1-yl)butane-2-ol, 98) (2R,3R)-3-(4-(5-cyanopyridine-2-yl)-1H-pyrazole-1-yl)-2-(2,4-difluorophenyl)-1-(1H-1,2,4-triazole-1-yl)butane-2-ol, 99) (2R,3R)-3-(4-(5-nitropyridine-2-yl)-1H-pyrazole-1-yl)-2-(2,4-difluorophenyl)-1-(1H-1,2,4-triazole-1-yl)butane-2-ol, 100) (2R,3R)-3-(4-(3-nitro-5-trifluoromethyl-pyridine-2-yl)-1H-pyrazole-1-yl)-2-(2,4-difluorophenyl)-1-(1H-1,2,4-triazole-1-yl)butane-2-ol, 101) (2R,3R)-3-(4-(5-cyano-3-methyl-pyridine-2-yl)-1H-pyrazole-1-yl)-2-(2,4-difluorophenyl)-1-(1H-1,2,4-triazole-1-yl)butane-2-ol, 102) (2R,3R)-3-(4-(5-chloro-3-methyl-pyridine-2-yl)-1H-pyrazole-1-yl)-2-(2,4-difluorophenyl)-1-(1H-1,2,4-triazole-1-yl)butane-2-ol, 103) (2R,3R)-3-(4-(3-fluoro-5-nitro-pyridine-2-yl)-1H-pyrazole-1-yl)-2-(2,4-difluorophenyl)-1-(1H-1,2,4-triazole-1-yl)butane-2-ol,
104) (2R,3R)-3-(4-(3-methyl-5-nitro-pyridine-2-yl)-1H-pyrazole-1-yl)-2-(2,4-difluorophenyl)-1-(1H-1,2,4-triazole-1-yl)butane-2-ol,
105) (2R,3R)-3-(4-(5-fluoro-pyridine-3-yl)-1H-pyrazole-1-yl)-2-(2,4-difluorophenyl)-1-(1H-1,2,4-triazole-1-yl)butane-2-ol,
106) (2R,3R)-3-(4-(5-chloro-pyridine-3-yl)-1H-pyrazole-1-yl)-2-(2,4-difluorophenyl)-1-(1H-1,2,4-triazole-1-yl)butane-2-ol,
107) (2R,3R)-3-(4-(5-cyano-pyridine-3-yl)-1H-pyrazole-1-yl)-2-(2,4-difluorophenyl)-1-(1H-1,2,4-triazole-1-yl)butane-2-ol,
108) (2R,3R)-3-(4-(4-fluoro-pyridine-3-yl)-1H-pyrazole-1-yl)-2-(2,4-difluorophenyl)-1-(1H-1,2,4-triazole-1-yl)butane-2-ol,
109) (2R,3R)-3-(4-(4-chloro-pyridine-3-yl)-1H-pyrazole-1-yl)-2-(2,4-difluorophenyl)-1-(1H-1,2,4-triazole-1-yl)butane-2-ol,
110) (2R,3R)-3-(4-(4-cyano-pyridine-3-yl)-1H-pyrazole-1-yl)-2-(2,4-difluorophenyl)-1-(1H-1,2,4-triazole-1-yl)butane-2-ol,
111) (2R,3R)-3-(4-(3-fluoro-pyridine-4-yl)-1H-pyrazole-1-yl)-2-(2,4-difluorophenyl)-1-(1H-1,2,4-triazole-1-yl)butane-2-ol,
112) (2R,3R)-3-(4-(3-chloro-pyridine-4-yl)-1H-pyrazole-1-yl)-2-(2,4-difluorophenyl)-1-(1H-1,2,4-triazole-1-yl)butane-2-ol,
113) (2R,3R)-3-(4-(3-cyano-pyridine-4-yl)-1H-pyrazole-1-yl)-2-(2,4-difluorophenyl)-1-(1H-1,2,4-triazole-1-yl)butane-2-ol,
114) (2R,3R)-3-(4-(3,5-difluoro-pyridine-4-yl)-1H-pyrazole-1-yl)-2-(2,4-difluorophenyl)-1-(1H-1,2,4-triazole-1-yl)butane-2-ol,
115) (2R,3R)-3-(4-(pyrimidin-4-yl)-1H-pyrazole-1-yl)-2-(2,4-difluorophenyl)-1-(1H-1,2,4-triazole-1-yl)butane-2-ol,
116) (2R,3R)-3-(4-(quinolin-4-yl)-1H-pyrazole-1-yl)-2-(2,4-difluorophenyl)-1-(1H-1,2,4-triazole-1-yl)butane-2-ol,
117) (2R,3R)-3-(4-(quinoxalin-2-yl)-1H-pyrazole-1-yl)-2-(2,4-difluorophenyl)-1-(1H-1,2,4-triazole-1-yl)butane-2-ol, and
118) (2R,3R)-3-(4-(benzofuran-2-yl)-1H-pyrazole-1-yl)-2-(2,4-difluorophenyl)-1-(1H-1,2,4-triazole-1-yl)butane-2-ol.

4. A method for preparing a compound represented by the following chemical formula 1 or a pharmaceutically acceptable salt thereof, comprising reacting a compound of the following chemical formula 2 with a compound of the following chemical formula 3 in the presence of a base:

Chemical Formula 1:

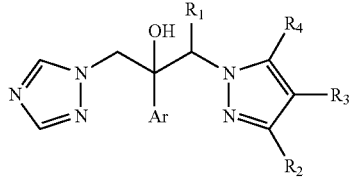

wherein,
Ar, $R_1$, $R_2$, $R_3$, $R_4$, $R_5$ and n are as defined in any one of claims 1 to 3;

Chemical Formula 2:

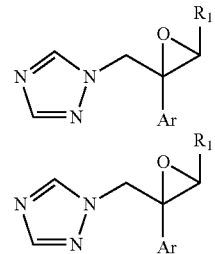

wherein, $R_1$ is as defined above,

Chemical Formula 3:

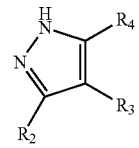

wherein, $R_2$, $R_3$ and $R_4$ are as defined above.

5. The method according to claim 4, wherein the base is an inorganic base selected from the group consisting of sodium hydride, potassium carbonate and sodium methoxide, or an organic base selected from the group consisting of triethylamine and 1,8-diazabicyclo(5,4,0)undec-7-ene.

6. An antifungal agent comprising the compound of any one of claims 1 to 3 or a pharmaceutically acceptable salt thereof, and a pharmaceutical vehicle.

7. A triazole derivative represented by the following chemical formula 1, or a pharmaceutically acceptable salt thereof:

Chemical Formula 1:

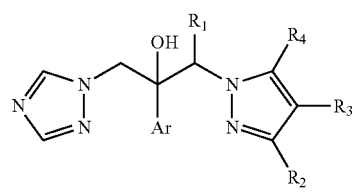

wherein,
Ar is phenyl substituted with at least one halogen or trifluoromethyl group;
$R_1$ is fluorine, or a $C_1$-$C_4$ lower alkyl;
$R_3$ is halogen; a $C_1$-$C_4$ lower alkyl; a $C_1$-$C_4$ alkoxy; a $C_1$-$C_4$ haloalkyl; a $C_3$-$C_6$ cycloalkyl;
a nitro; a cyano; an amino; a hydroxy; a $C_6$-$C_{20}$ aryl, non-substituted or substituted with at least one selected from the group consisting of a $C_1$-$C_4$ lower alkyl, a $C_1$-$C_4$ alkoxy, a halogen, a cyano, a nitro, a $C_1$-$C_4$ haloalkyl, a $C_1$-$C_4$ haloalkoxy, morpholine, pyrrolidine, piperidine,

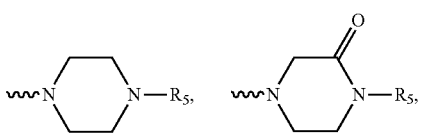

-continued

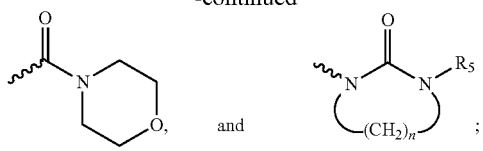

or a $C_6$-$C_{20}$ heteroaryl, non-substituted or substituted with at least one substituent selected from the group consisting of a $C_1$-$C_4$ lower alkyl, a $C_1$-$C_4$ alkoxy, a halogen, a cyano, a nitro, a $C_1$-$C_4$ haloalkyl, and a $C_1$-$C_4$ haloalkoxy, $R_2$ and $R_4$ may be different or the same and are hydrogen; a halogen; a $C_1$-$C_4$ lower alkyl; a $C_1$-$C_4$ alkoxy; a $C_1$-$C_4$ haloalkyl; a $C_3$-$C_6$ cycloalkyl; a nitro; a cyano; an amino; a hydroxy; a $C_6$-$C_{20}$ aryl, non-substituted or substituted with at least one selected from the group consisting of a $C_1$-$C_4$ lower alkyl, a $C_1$-$C_4$ alkoxy, a halogen, a cyano, a nitro, a $C_1$-$C_4$ haloalkyl, a $C_1$-$C_4$ haloalkoxy, morpholine, pyrrolidine, piperidine,

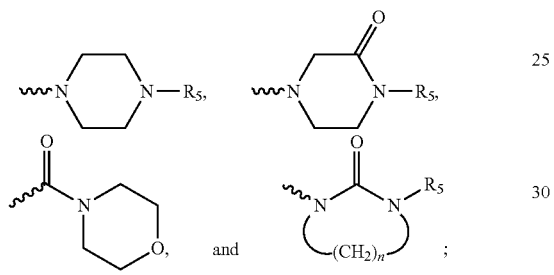

or a $C_6$-$C_{20}$ heteroaryl, non-substituted or substituted with at least one substituent selected from the group consisting of a $C_1$-$C_4$ lower alkyl, a $C_1$-$C_4$ alkoxy, a halogen, a cyano, a nitro, a $C_1$-$C_4$ haloalkyl, and a $C_1$-$C_4$ haloalkoxy, $R_5$ is hydrogen, a $C_1$-$C_4$ alkyl, a $C_1$-$C_4$ alkoxy or a $C_1$-$C_5$ hydroxy alkyl, and n is an integer from 1 to 3.

8. A triazole derivative represented by the following chemical formula 1, or a pharmaceutically acceptable salt thereof:

Chemical Formula 1:

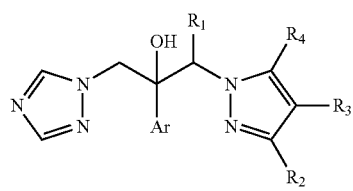

wherein,

Ar is phenyl substituted with at least one halogen or trifluoromethyl group;

$R_1$ is fluorine, or a $C_1$-$C_4$ lower alkyl;

$R_4$ is a halogen; a $C_1$-$C_4$ lower alkyl; a $C_1$-$C_4$ alkoxy; a $C_1$-$C_4$ haloalkyl; a $C_3$-$C_6$ cycloalkyl; a nitro; a cyano; an amino; a hydroxy; a $C_6$-$C_{20}$ aryl, non-substituted or substituted with at least one selected from the group consisting of a $C_1$-$C_4$ lower alkyl, a $C_1$-$C_4$ alkoxy, a halogen, a cyano, a nitro, a $C_1$-$C_4$ haloalkyl, a $C_1$-$C_4$ haloalkoxy, morpholine, pyrrolidine, piperidine,

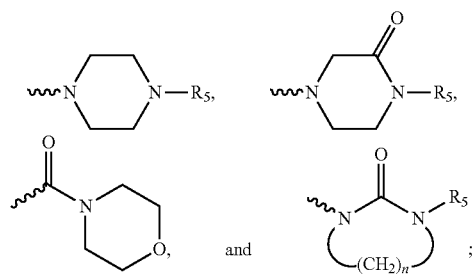

or a $C_6$-$C_{20}$ heteroaryl, non-substituted or substituted with at least one substituent selected from the group consisting of a $C_1$-$C_4$ lower alkyl, a $C_1$-$C_4$ alkoxy, a halogen, a cyano, a nitro, a $C_1$-$C_4$ haloalkyl, and a $C_1$-$C_4$ haloalkoxy, $R_2$ and $R_3$ may be different or the same and are hydrogen; a halogen; a $C_1$-$C_4$ lower alkyl; a $C_1$-$C_4$ alkoxy; a $C_1$-$C_4$ haloalkyl; a $C_3$-$C_6$ cycloalkyl; a nitro; a cyano; an amino; a hydroxy; a $C_6$-$C_{20}$ aryl, non-substituted or substituted with at least one selected from the group consisting of a $C_1$-$C_4$ lower alkyl, a $C_1$-$C_4$ alkoxy, a halogen, a cyano, a nitro, a $C_1$-$C_4$ haloalkyl, a $C_1$-$C_4$ haloalkoxy, morpholine, pyrrolidine, piperidine,

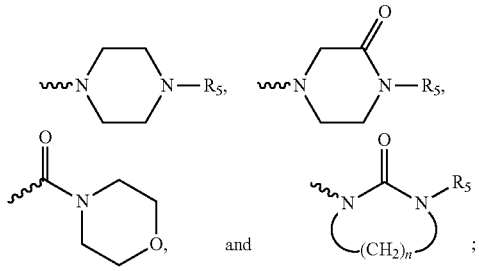

or a $C_6$-$C_{20}$ heteroaryl, non-substituted or substituted with at least one substituent selected from the group consisting of a $C_1$-$C_4$ lower alkyl, a $C_1$-$C_4$ alkoxy, a halogen, a cyano, a nitro, a $C_1$-$C_4$ haloalkyl, and a $C_1$-$C_4$ haloalkoxy, $R_5$ is hydrogen, a $C_1$-$C_4$ alkyl, a $C_1$-$C_4$ alkoxy or a $C_1$-$C_5$ hydroxy alkyl, and n is an integer from 1 to 3.

9. The triazole derivative or pharmaceutically acceptable salt thereof according to claim 7, wherein Ar is phenyl substituted with at least one halogen, $R_1$ is a $C_1$-$C_4$ lower alkyl, $R_3$ is a $C_1$-$C_4$ lower alkyl; a $C_1$-$C_4$ haloalkyl; a nitro; a cyano; an amino; a hydroxy;

phenyl, non-substituted or substituted with at least one selected from the group consisting of a $C_1$-$C_4$ lower alkyl, a $C_1$-$C_4$ alkoxy, a halogen, a cyano, a nitro, trifluoromethyl, trifluoromethoxy, morpholine, pyrrolidine,

or heteroaryl selected from among pyridine, pyrimidine, quinoline, quinoxaline and benzofuran, said heteroaryl being non-substituted or substituted with at least one selected from the group consisting of a $C_1$-$C_4$ lower alkyl, a $C_1$-$C_4$ alkoxy, a halogen, a cyano, a nitro, trifluoromethyl and trifluoromethoxy, $R_2$ and $R_4$ may be different or the same and are each hydrogen; a $C_1$-$C_4$ lower alkyl; a $C_1$-$C_4$ haloalkyl; a nitro; a cyano; an amino; a hydroxy; a phenyl, non-substituted or substituted with at least one selected from the group consisting of a $C_1$-$C_4$ lower alkyl, a $C_1$-$C_4$ alkoxy, a halogen, a cyano, a nitro, trifluoromethyl, trifluoromethoxy, morpholine, pyrrolidine,

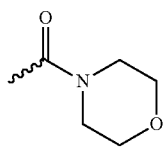 and 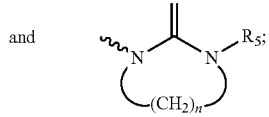

or heteroaryl selected from among pyridine, pyrimidine, quinoline, quinoxaline and benzofuran, said heteroaryl being non-substituted or substituted with at least one selected from the group consisting of a $C_1$-$C_4$ lower alkyl, a $C_1$-$C_4$ alkoxy, a halogen, a cyano, a nitro, trifluoromethyl and trifluoromethoxy, $R_5$ is hydrogen, a $C_1$-$C_4$ alkyl, or $C_1$-$C_5$ hydroxy alkyl, and n is an integer of 2 or 3.

10. The triazole derivative or pharmaceutically acceptable salt thereof according to claim 8, wherein Ar is phenyl substituted with at least one halogen, $R_1$ is a $C_1$-$C_4$ lower alkyl, $R_4$ is a $C_1$-$C_4$ lower alkyl; a $C_1$-$C_4$ haloalkyl; a nitro; a cyano; an amino; a hydroxy;

phenyl, non-substituted or substituted with at least one selected from the group consisting of a $C_1$-$C_4$ lower alkyl, a $C_1$-$C_4$ alkoxy, a halogen, a cyano, a nitro, trifluoromethyl, trifluoromethoxy, morpholine, pyrrolidine,

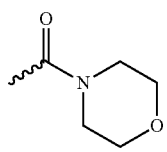 and 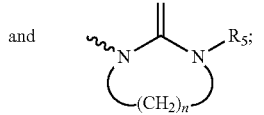

or heteroaryl selected from among pyridine, pyrimidine, quinoline, quinoxaline and benzofuran, said heteroaryl being non-substituted or substituted with at least one selected from the group consisting of a $C_1$-$C_4$ lower alkyl, a $C_1$-$C_4$ alkoxy, a halogen, a cyano, a nitro, trifluoromethyl and trifluoromethoxy, $R_2$ and $R_3$ may be different or the same and are each hydrogen; a $C_1$-$C_4$ lower alkyl; a $C_1$-$C_4$ haloalkyl; a nitro; a cyano; an amino; a hydroxy; phenyl, non-substituted or substituted with at least one selected from the group consisting of a $C_1$-$C_4$ lower alkyl, a $C_1$-$C_4$ alkoxy, a halogen, a cyano, a nitro, trifluoromethyl, trifluoromethoxy, morpholine, pyrrolidine,

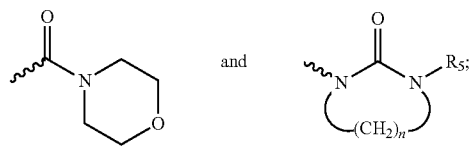

or heteroaryl selected from among pyridine, pyrimidine, quinoline, quinoxaline and benzofuran, said heteroaryl being non-substituted or substituted with at least one selected from the group consisting of a $C_1$-$C_4$ lower alkyl, a $C_1$-$C_4$ alkoxy, a halogen, a cyano, a nitro, trifluoromethyl and trifluoromethoxy, $R_5$ is hydrogen, a $C_1$-$C_4$ alkyl, or a $C_1$-$C_5$ hydroxy alkyl, and n is an integer of 2 or 3.

11. A method for preparing a compound represented by the following chemical formula 1 or a pharmaceutically acceptable salt thereof, comprising reacting a compound of the following chemical formula 2 with a compound of the following chemical formula 3 in the presence of a base:

Chemical Formula 1:

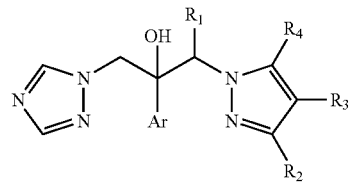

wherein,

Ar, $R_1$, $R_2$, $R_3$, and $R_4$ are as defined in any one of claims 7 to 10;

Chemical Formula 2:

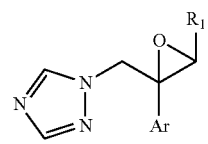

wherein, $R_1$ and Ar are as defined above,

Chemical Formula 3:

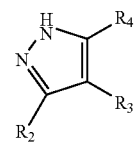

wherein, $R_2$, $R_3$ and $R_4$ are as defined above.

12. The method according to claim 11, wherein the base is an inorganic base selected from the group consisting of sodium hydride, potassium carbonate and sodium methoxide, or an organic base selected from the group consisting of triethylamine and 1,8-diazabicyclo(5,4,0)undec-7-ene.

13. An antifungal agent comprising the compound of any one of claims 7 to 10 or a pharmaceutically acceptable salt thereof, and a pharmaceutical vehicle.

* * * * *